(12) United States Patent
Uchiyama et al.

(10) Patent No.: US 7,711,408 B2
(45) Date of Patent: May 4, 2010

(54) MEDICAL DEVICE GUIDANCE SYSTEM

(75) Inventors: Akio Uchiyama, Yokohama (JP); Hironao Kawano, Hino (JP); Kenichi Arai, Shiogama (JP); Kazushi Ishiyama, Sendai (JP); Masahiko Sendoh, Sendai (JP)

(73) Assignee: Olympus Corporation, Tokyo (JP)

( * ) Notice: Subject to any disclaimer, the term of this patent is extended or adjusted under 35 U.S.C. 154(b) by 952 days.

(21) Appl. No.: 11/230,201

(22) Filed: Sep. 19, 2005

(65) Prior Publication Data
US 2006/0063974 A1   Mar. 23, 2006

(30) Foreign Application Priority Data
Sep. 21, 2004   (JP) .............................. 2004-273936

(51) Int. Cl.
*A61B 5/05* (2006.01)
(52) U.S. Cl. ................... 600/424; 600/423; 600/410; 600/434; 600/421; 600/407; 324/307; 436/173
(58) Field of Classification Search ................ None
See application file for complete search history.

(56) References Cited

U.S. PATENT DOCUMENTS

| 5,469,840 | A | * | 11/1995 | Tanii et al. | .................. 600/117 |
| 6,014,581 | A | * | 1/2000 | Whayne et al. | ............. 600/523 |
| 6,471,637 | B1 | * | 10/2002 | Green et al. | ................. 600/109 |
| 2003/0181788 | A1 | * | 9/2003 | Yokoi et al. | ................. 600/160 |
| 2003/0229268 | A1 | | 12/2003 | Uchiyama et al. | |
| 2004/0236180 | A1 | | 11/2004 | Uchiyama et al. | |

FOREIGN PATENT DOCUMENTS

| EP | 1 591 058 A1 | 11/2005 |
| JP | 2001-179700 | 7/2001 |
| JP | 2002-187100 | 7/2002 |
| JP | 2003-275170 | 9/2003 |
| JP | 2004-229922 | 8/2004 |
| JP | 2004-255174 | 9/2004 |
| WO | WO 2004/069043 A1 | 8/2004 |

OTHER PUBLICATIONS

Supplementary European Search Report dated Jan. 13, 2010.

* cited by examiner

*Primary Examiner*—Long V Le
*Assistant Examiner*—Joel F Brutus
(74) *Attorney, Agent, or Firm*—Scully, Scott, Murphy & Presser, P.C.

(57) ABSTRACT

The present invention realizes a medical device guidance system capable of improving propulsion control characteristic. The capsule guidance system 1 includes a rotating electromagnetic field generating device 4 for generating a rotating electromagnetic field for applying from the outside of a subject into the subject; a capsule 3 to be inserted into the body cavity of the subject; a magnet 16 provided in this capsule 3 and acting on the rotating electromagnetic field generated by the rotating electromagnetic field generating device 4; a spiral projection portion 12 provided on the outer peripheral surface of the capsule 3 and converting the rotational movement generated by the magnet 16 into a thrust; a controller 6 for controlling the rotating electromagnetic field generating device 4 to continuously change the state of the rotating electromagnetic field generated by rotating electromagnetic field generating device 4; and a capsule rotational direction pattern generator 41 for interchanging the rotational directions of the rotating electromagnetic field generated by the rotating electromagnetic field generating device 4 for each set rotational direction.

15 Claims, 21 Drawing Sheets

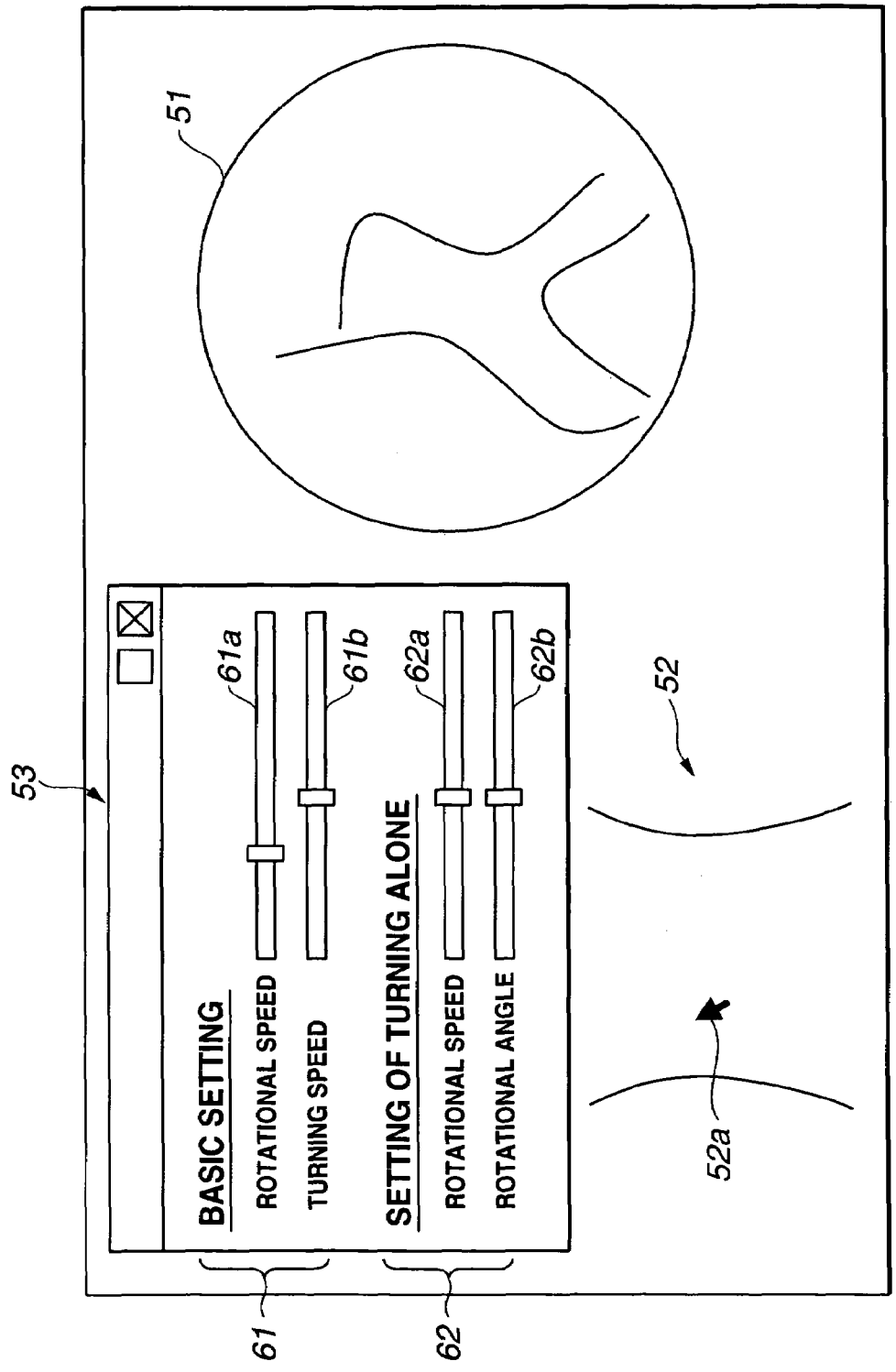

PITCH: CONSTANT   a = b = c

L: LENGTH OF CYLINDRICAL SECTION
r: RADIUS OF CYLINDRICAL SECTION
n: NUMBER OF THREADS (NATURAL NUMBER)
D: SPIRAL INTERVAL

MEDICAL DEVICE GUIDANCE SYSTEM

This application claims benefit of Japanese application No. 2004-273936 filed on Sep. 21, 2004, the contents of which are incorporated by this reference.

BACKGROUND OF THE INVENTION

1. Field of the Invention

The present invention relates to a medical device guidance system suitable for rotating, propelling, and guiding a medical device main body inserted in a body cavity.

2. Description of the Related Art

Conventional examples of systems for propelling a micromachine in a subject by a rotating magnetic field are set forth in Japanese Unexamined Patent Application Publication Nos. 2001-179700 and 2002-187100. These conventional examples each disclose a movement control system for a movable micromachine, the system including magnetic field generating sections for generating a rotating magnetic field; a robot main body rotating under this rotating magnetic field and obtaining a thrust by the rotation; a position detecting section for detecting the position of the robot main body; and magnetic field modifying means for modifying the orientation of the rotating magnetic field generated by the magnetic field generating sections, for directing the robot main body toward the direction such that the robot main body reaches a target destination, based on the position of the robot main body, detected by the position detecting section.

On the other hand, a capsule type medical device, typified by a capsule endoscope, is now applied to a gastrointestinal organ (mainly, small intestine).

Such being the case, as set forth in Japanese Unexamined Patent Application Publication No. 2003-275170, a capsule type medical device guidance system that guides a medical device by providing a guidance mechanism for this capsule type medical device, is disclosed.

Furthermore, Japanese Unexamined Patent Application Publication No. 2004-229922 discloses a capsule endoscope having a spiral structure section and being rotationally propelled. In this Japanese Unexamined Patent Application Publication No. 2004-229922, studies about the height of a spiral, the pitch thereof, the number of threads of the spiral are disclosed.

SUMMARY OF THE INVENTION

A medical device guidance system according to the present invention includes a rotating electromagnetic field generating device for generating a rotating electromagnetic field for applying from the outside of a subject into the subject; a medical device main body inserted into a body cavity of the subject; an electromagnetic field response section provided in the medical device main body, and acting on the rotating electromagnetic field generated by the rotating electromagnetic field generating device; a spiral structure section provided on the outer surface of the medical device main body, and converting a rotational movement generated by the electromagnetic field response section into a thrust; a setting device for inputting setting data for guiding the medical device main body under a desired setting condition; an electromagnetic field pattern signal generating section for generating an electromagnetic field pattern signal based on the setting data inputted into the setting device; and a control section for controlling the rotating electromagnetic field generating device to continuously change the state of the rotating electromagnetic field, based on the electromagnetic field pattern signal.

BRIEF DESCRIPTION OF THE DRAWINGS

FIG. 13 is an example of a display device and setting menu.

DETAILED DESCRIPTION OF THE PREFERRED EMBODIMENTS

Hereinafter, an embodiment according to the present invention will be described with reference to the drawings.

Figure 1:
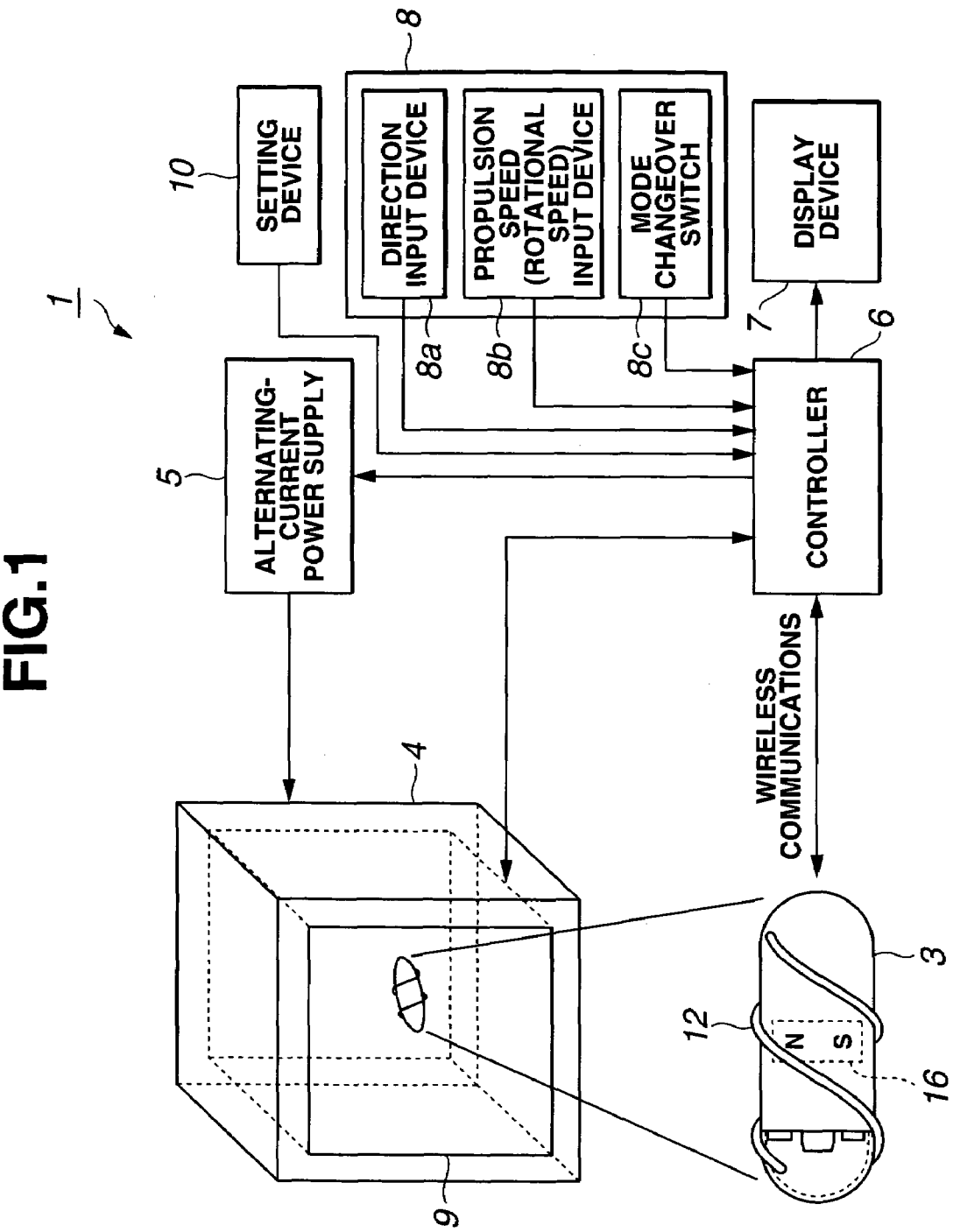
FIG. 1 is a schematic block diagram showing the overall configuration of a medical device guidance system according to an embodiment of the present invention.
Figure 2:
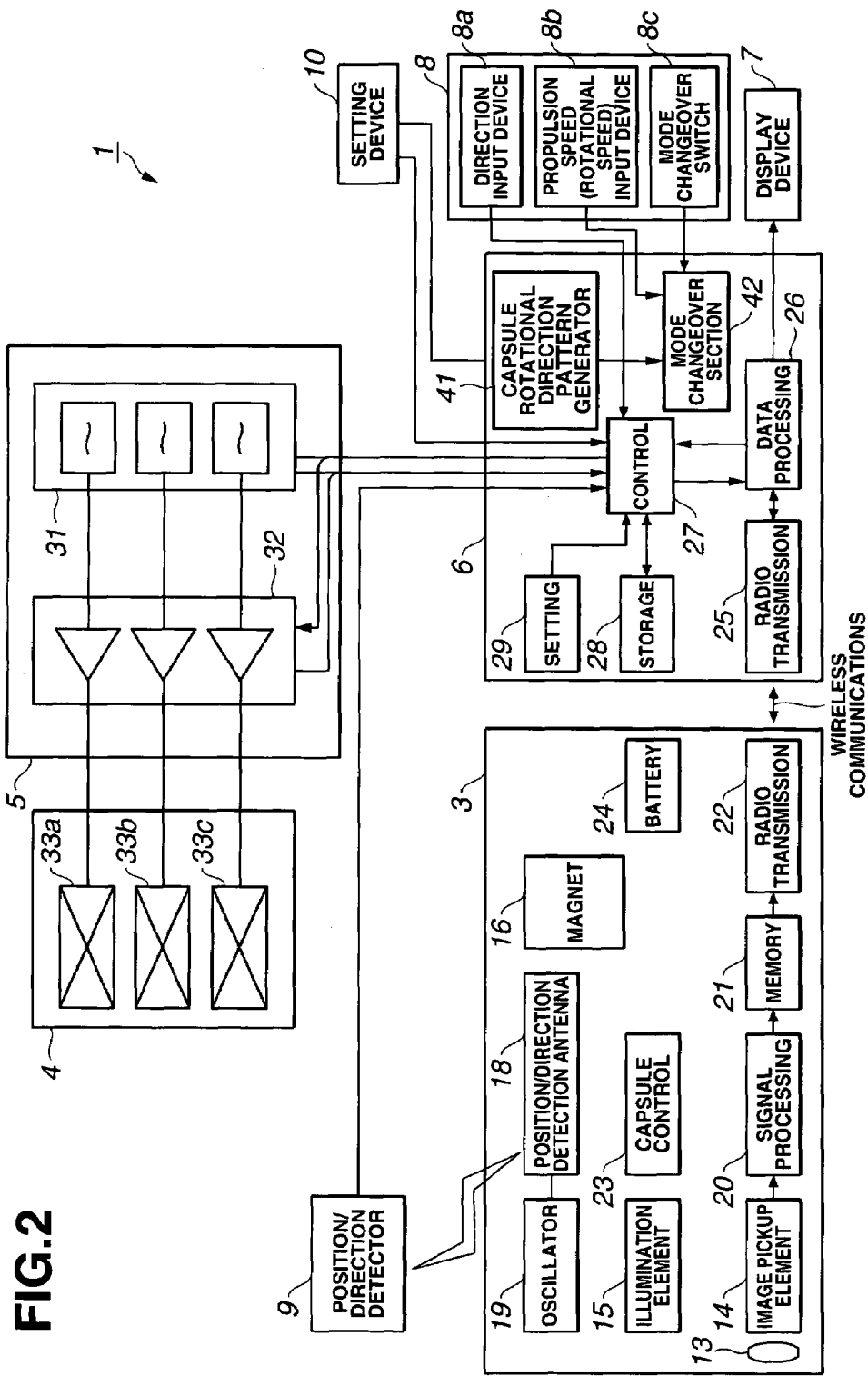
FIG. 2 is a block diagram showing a more detailed configuration than that in FIG. 1.
Figure 3:
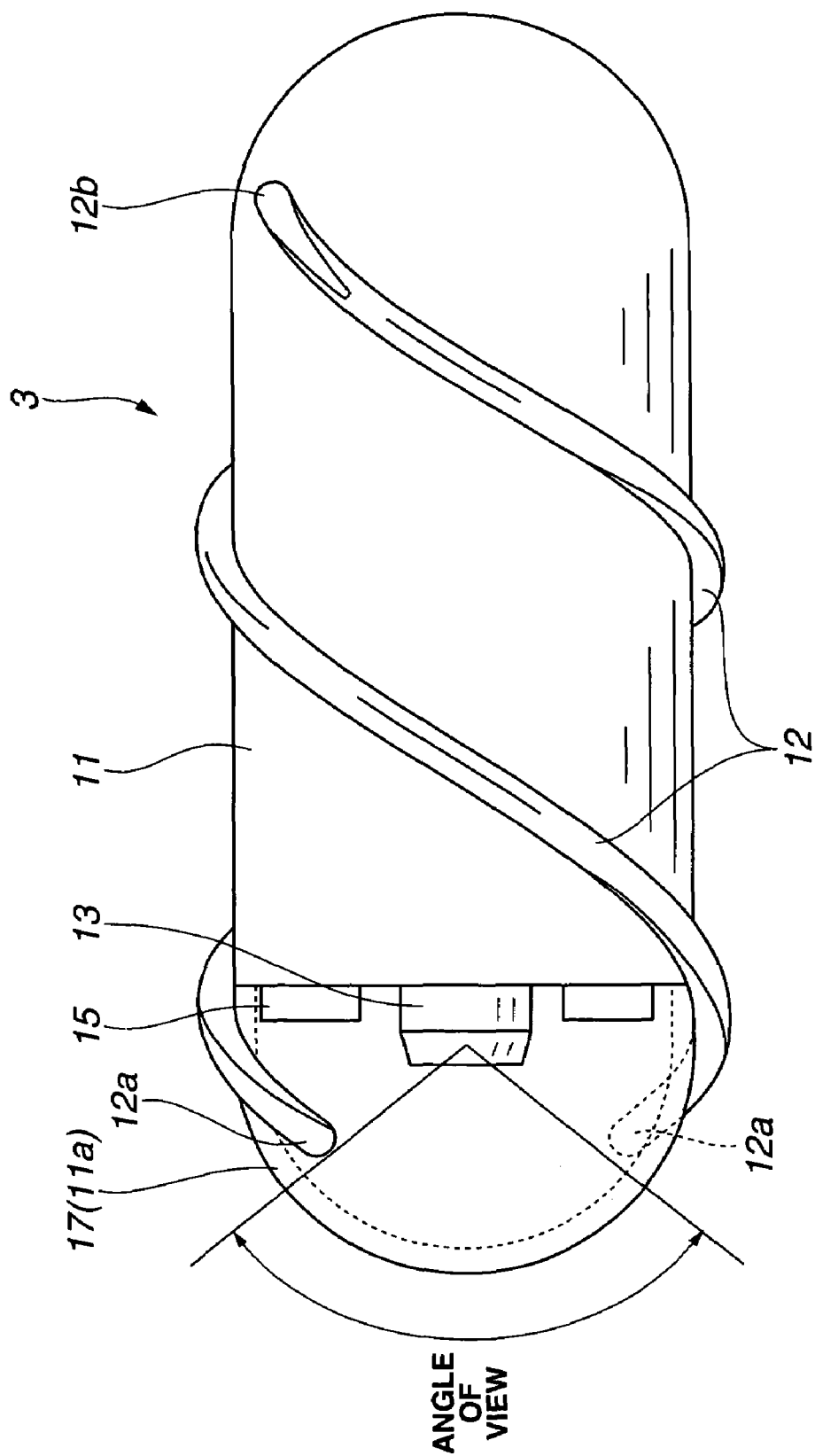
FIG. 3 is a side view showing the outer appearance of the capsule medical device main body.
Figure 4:
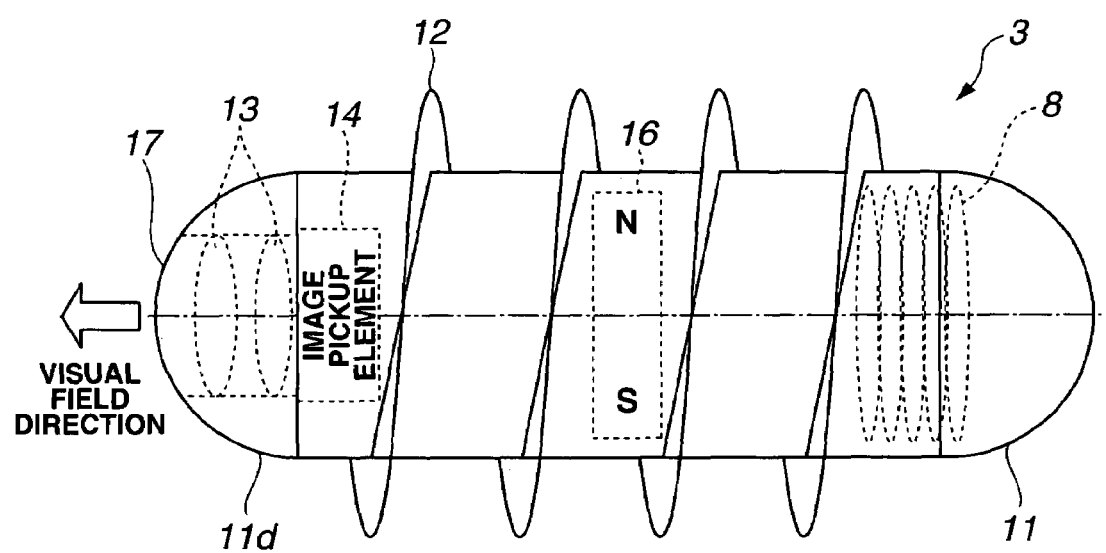
FIG. 4 is an explanatory side view of the main body of the capsule medical device.
Figure 5:
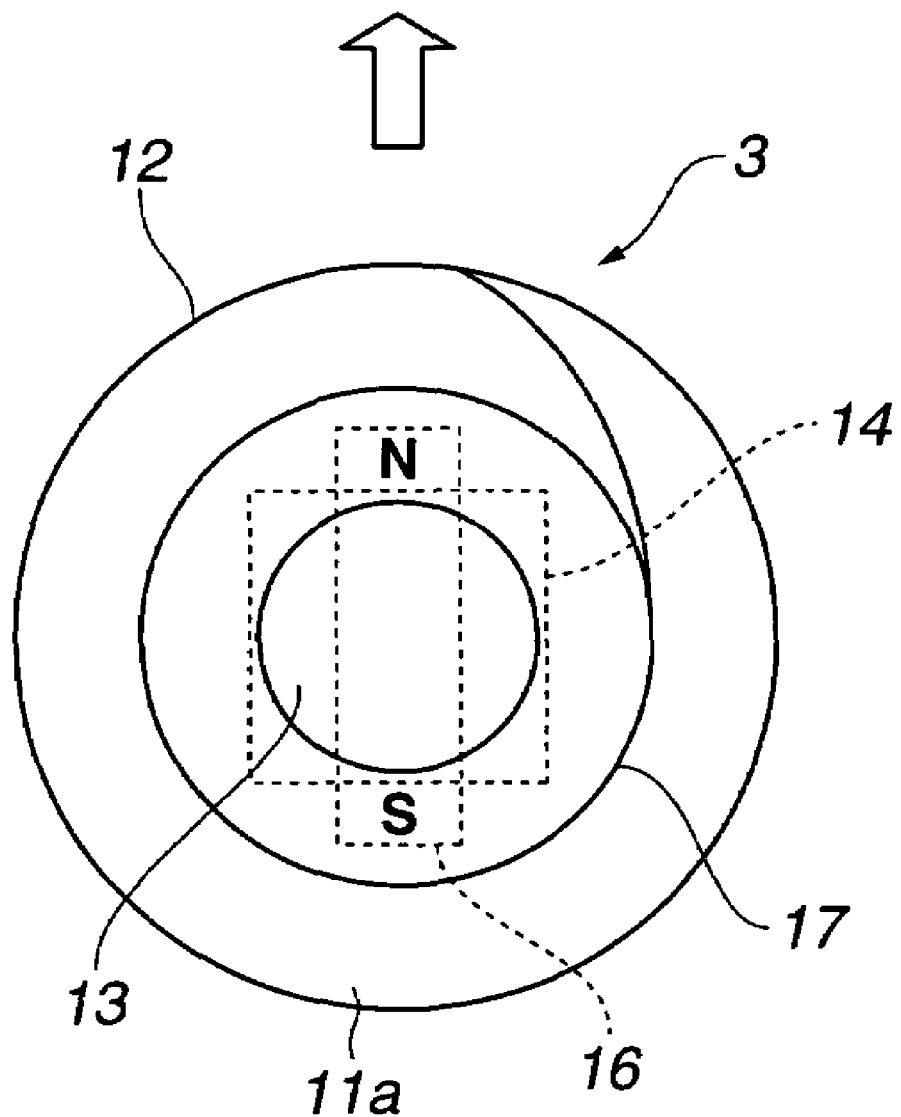
FIG. 5 is an explanatory front view of the main body of the capsule medical device in FIG. 4.
Figure 6:
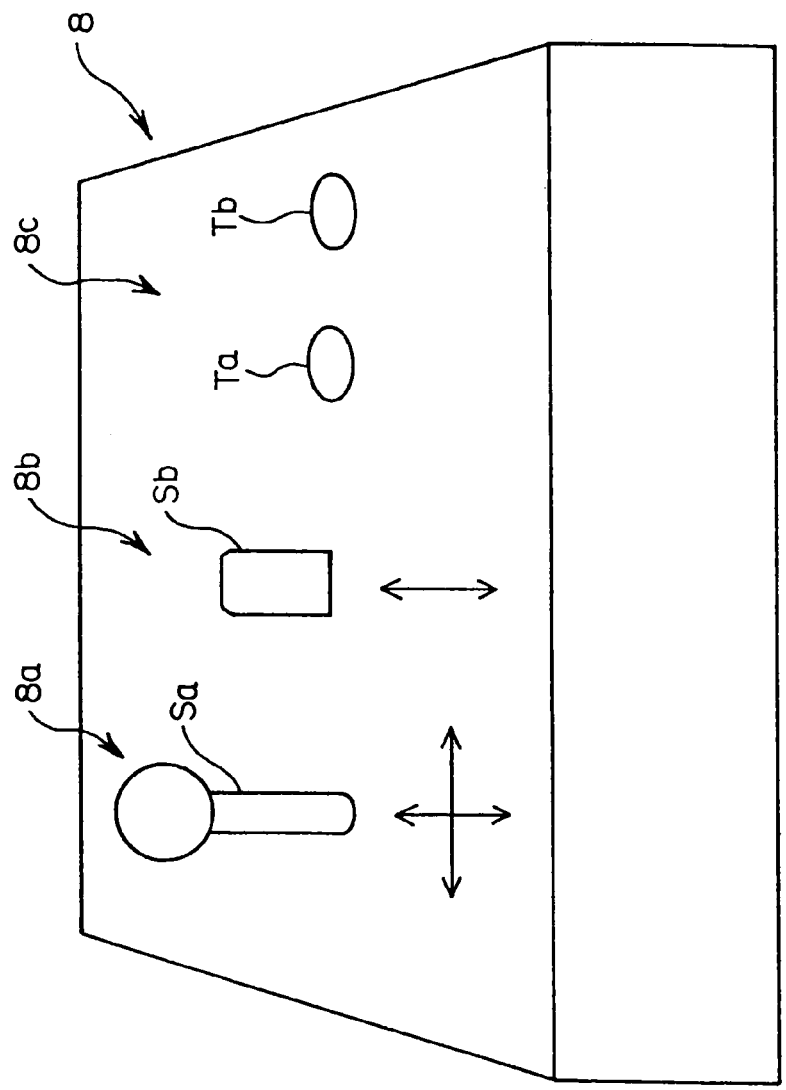
FIG. 6 is a schematic configuration view of an operation input device.
Figure 7:
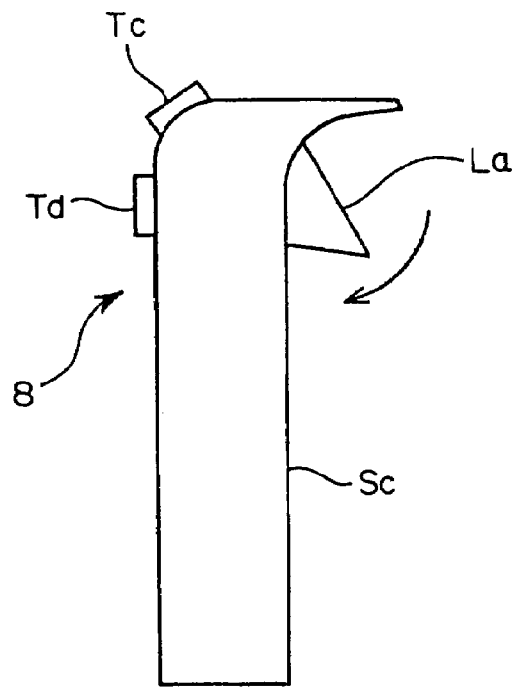
FIG. 7 is a schematic configuration view of a modification of the operation input device.
Figure 8:
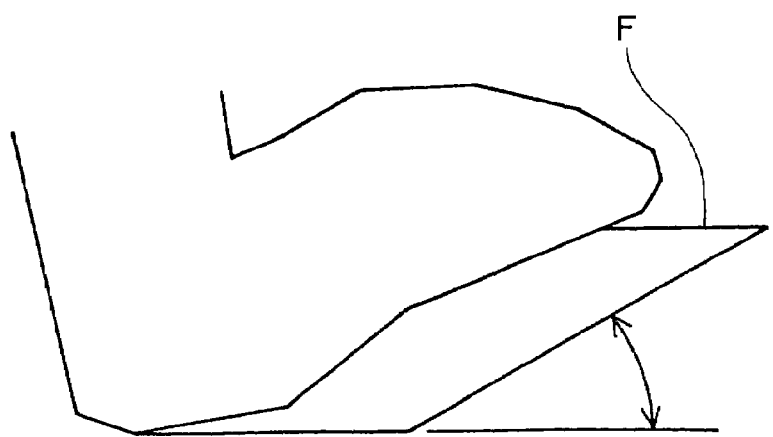
FIG. 8 is a schematic configuration view of a modification of a stick in FIG. 6.
Figure 9A:
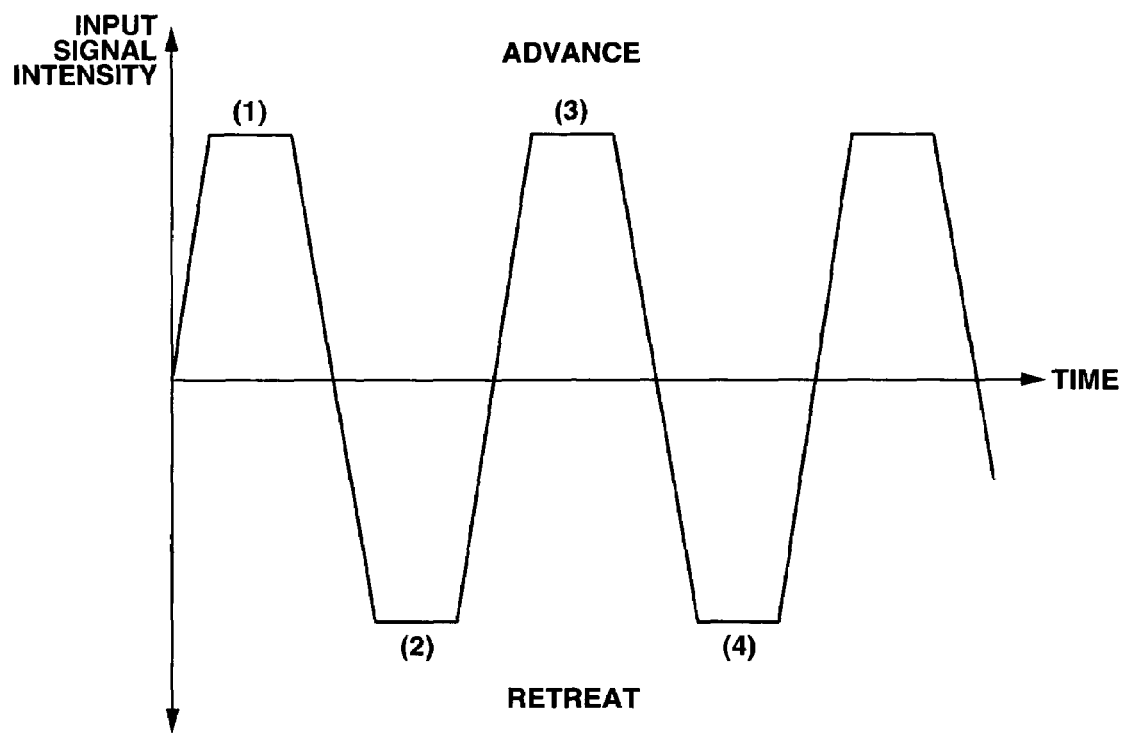
FIG. 9A is a graph showing an example of signal waveform generated by a capsule rotational direction pattern generator.
Figure 9B:
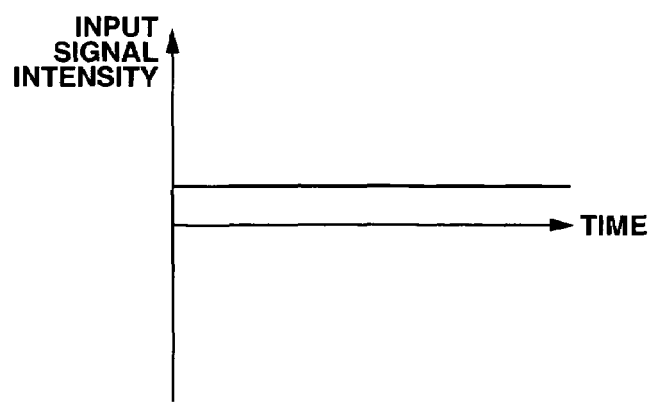
FIG. 9B is a graph showing another example of signal waveform generated by the capsule rotational direction pattern generator.
Figure 10:
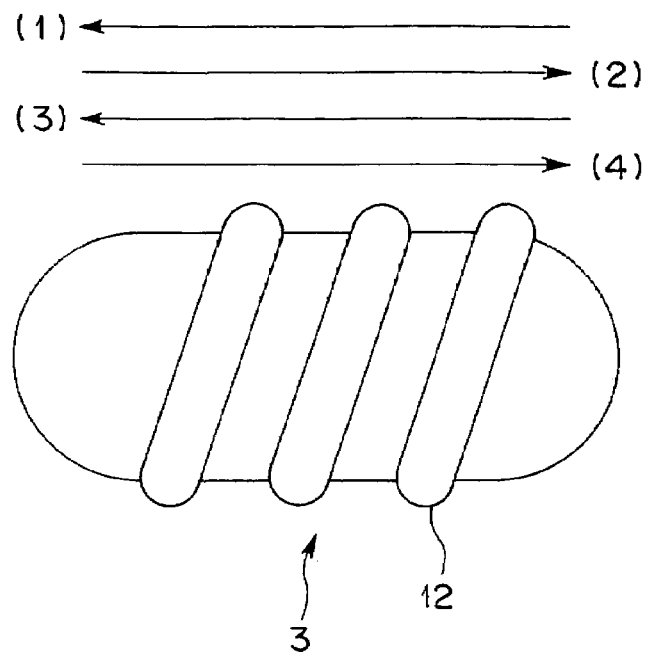
FIG. 10 is an explanatory side view of the capsule medical device main body when it repeats an advance and a retreat based on the signal in FIG. 9A.
Figure 12:
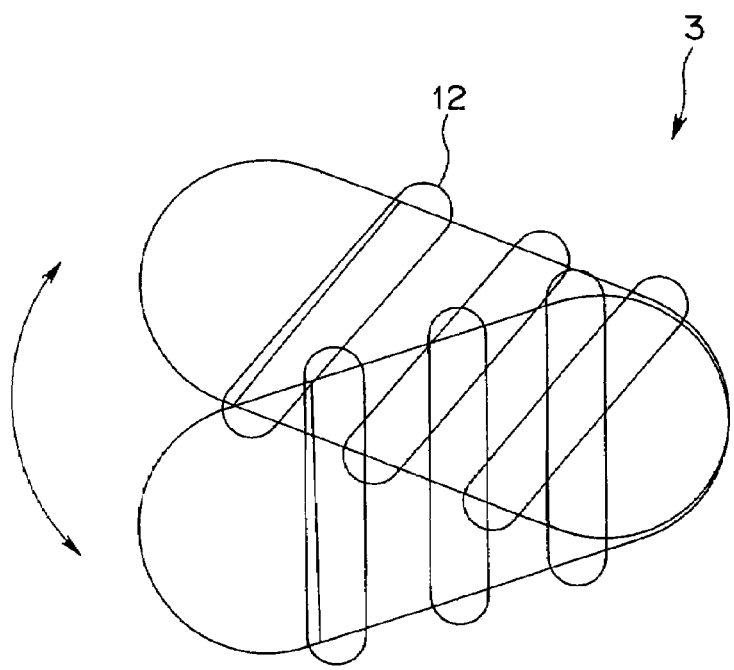
FIG. 12 is a schematic explanatory view showing of a state of the capsule medical device main body when making a turning motion based on the advance and retreat shown in FIG. 10.
Figure 11:
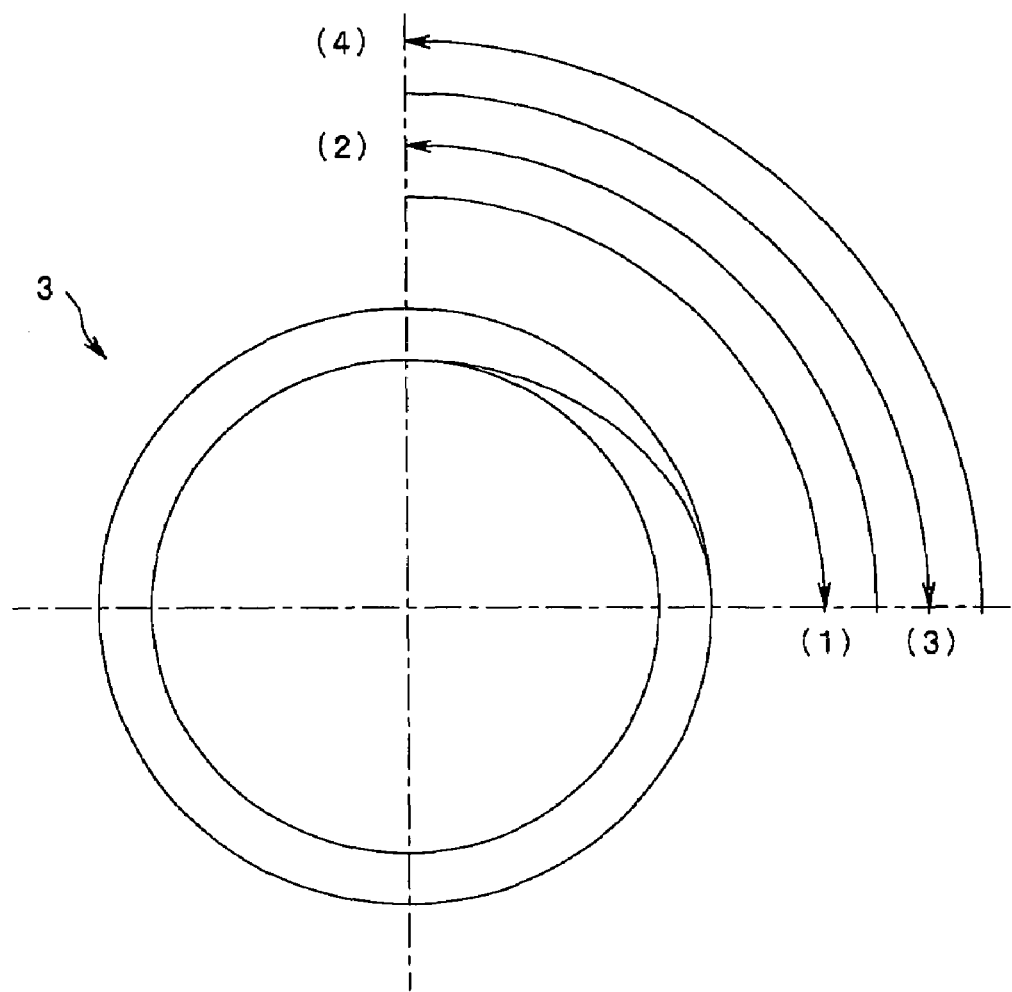
FIG. 11 is an explanatory front view of the main body of the capsule medical device in FIG. 10.
Figure 14:
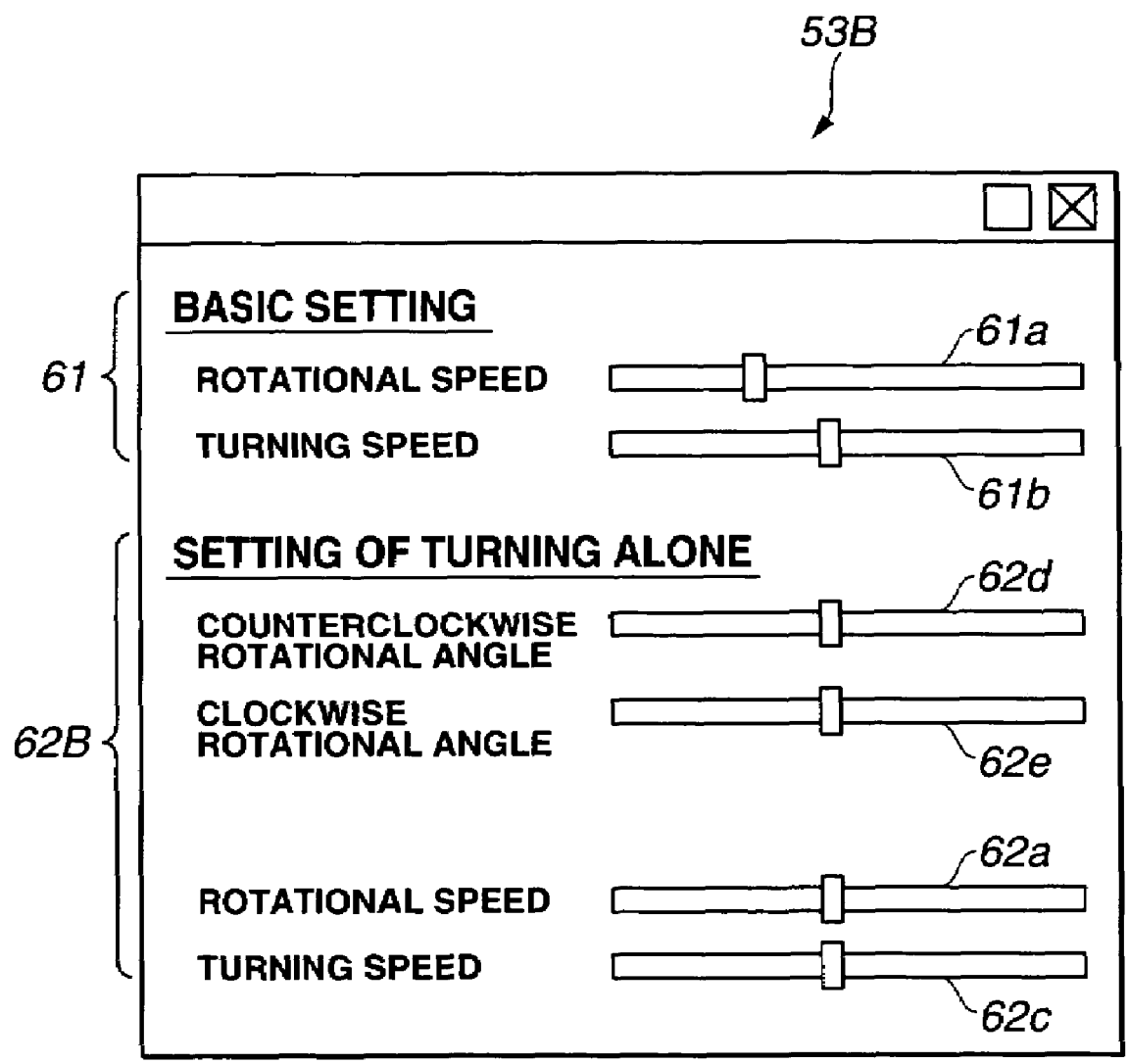
FIG. 14 is a modification of the setting menu in FIG. 13.
Figure 15:
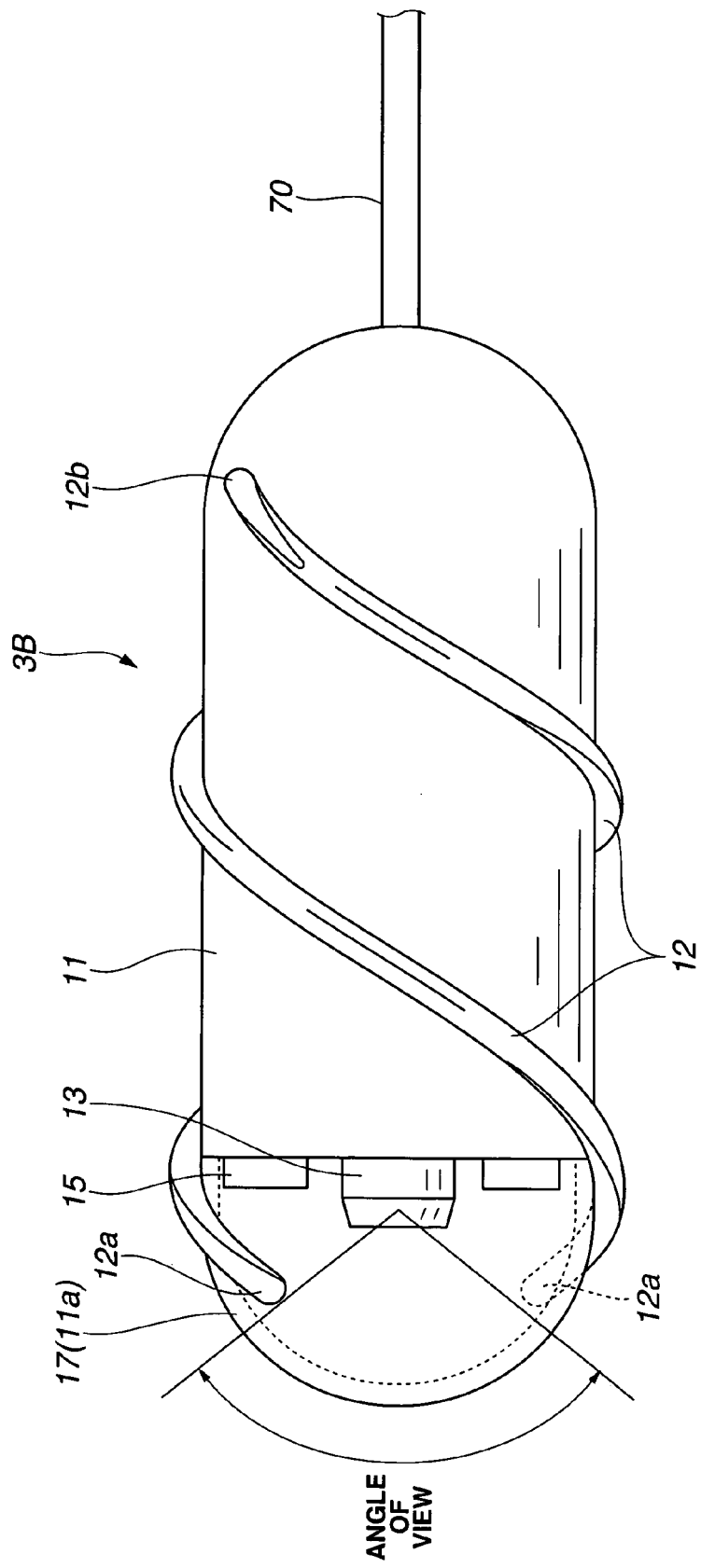
FIG. 15 is a side view showing the outer appearance of a cable-equipped medical device having a flexible tube rotatably installed at its rear end.
Figure 16:
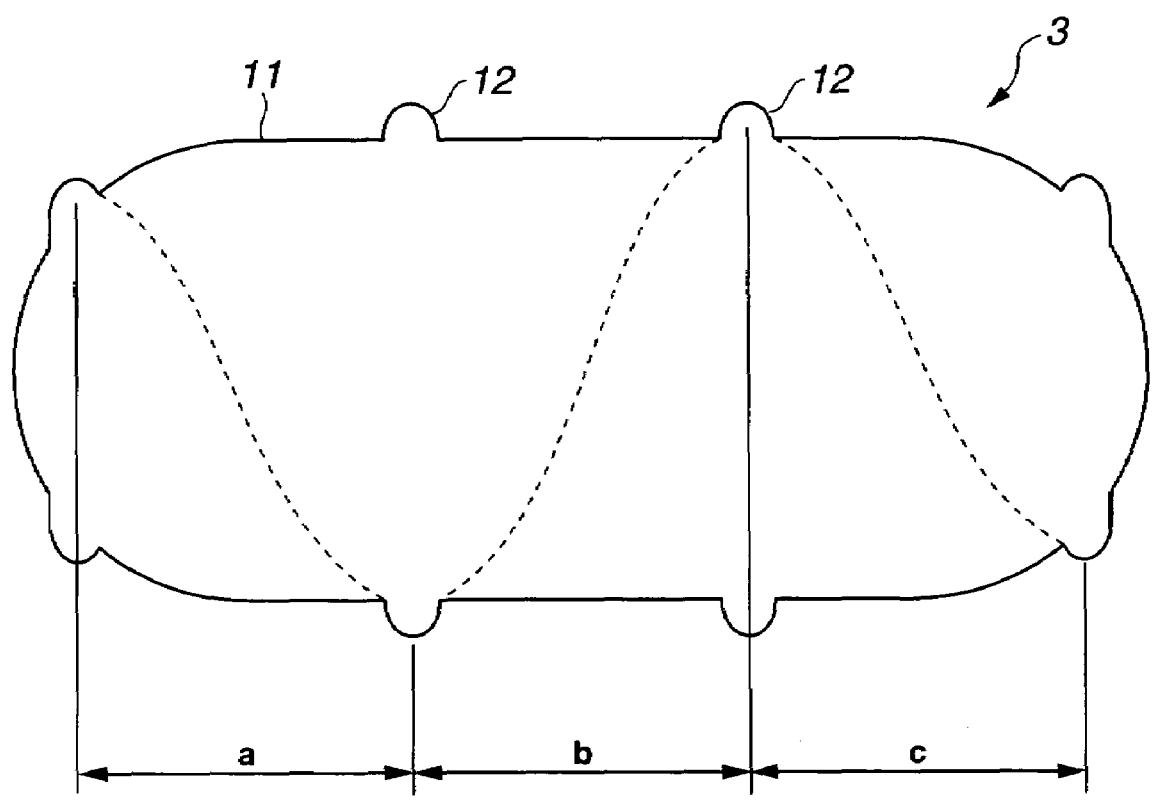
FIG. 16 is a schematic side view showing a capsule medical device on which the pitch of a spiral projection is the same at the central portion, front end side, and rear end side.
Figure 17:
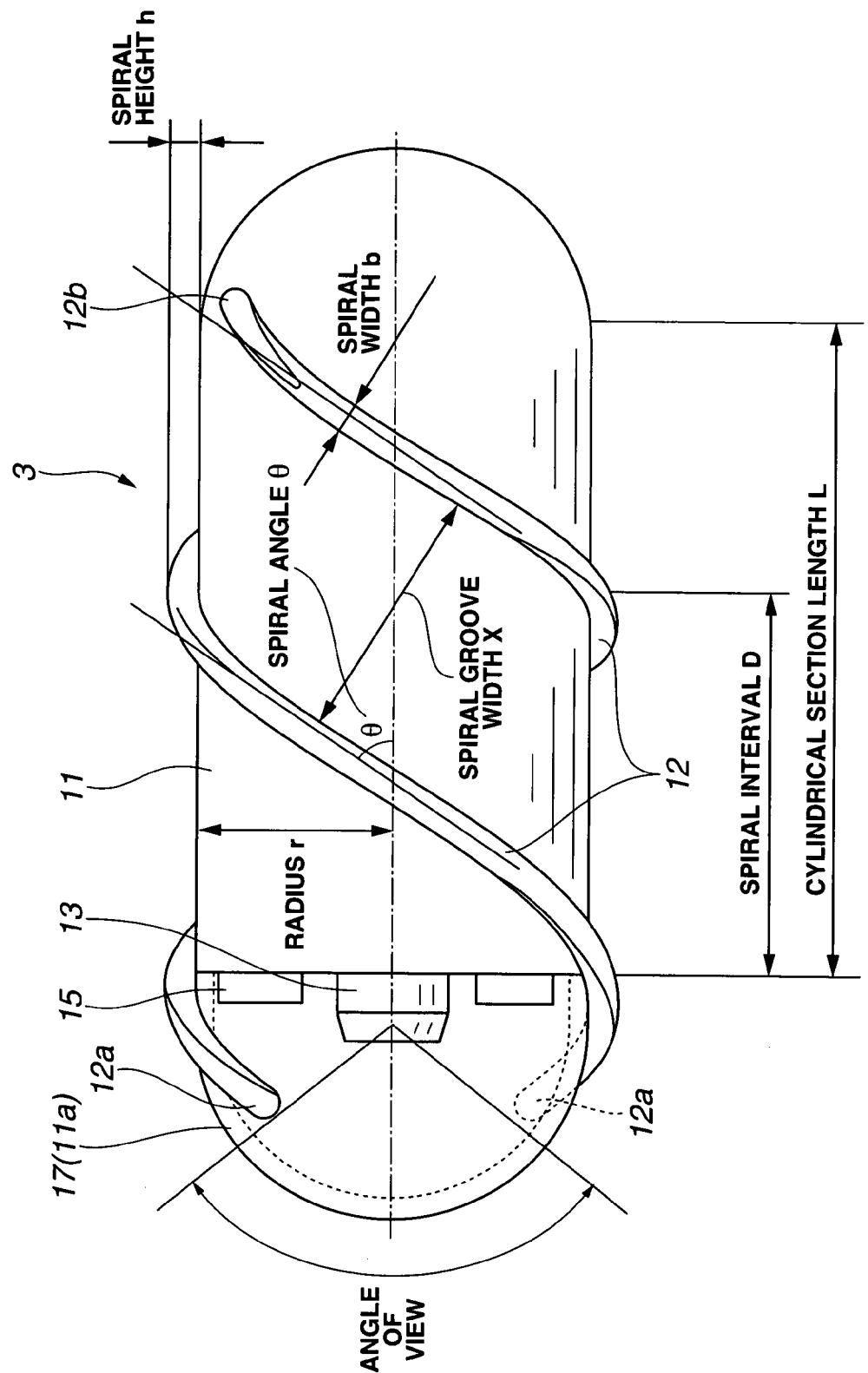
FIG. 17 is an explanatory side view showing parameters of the spiral structure section of the medical device guidance system.
Figure 18:
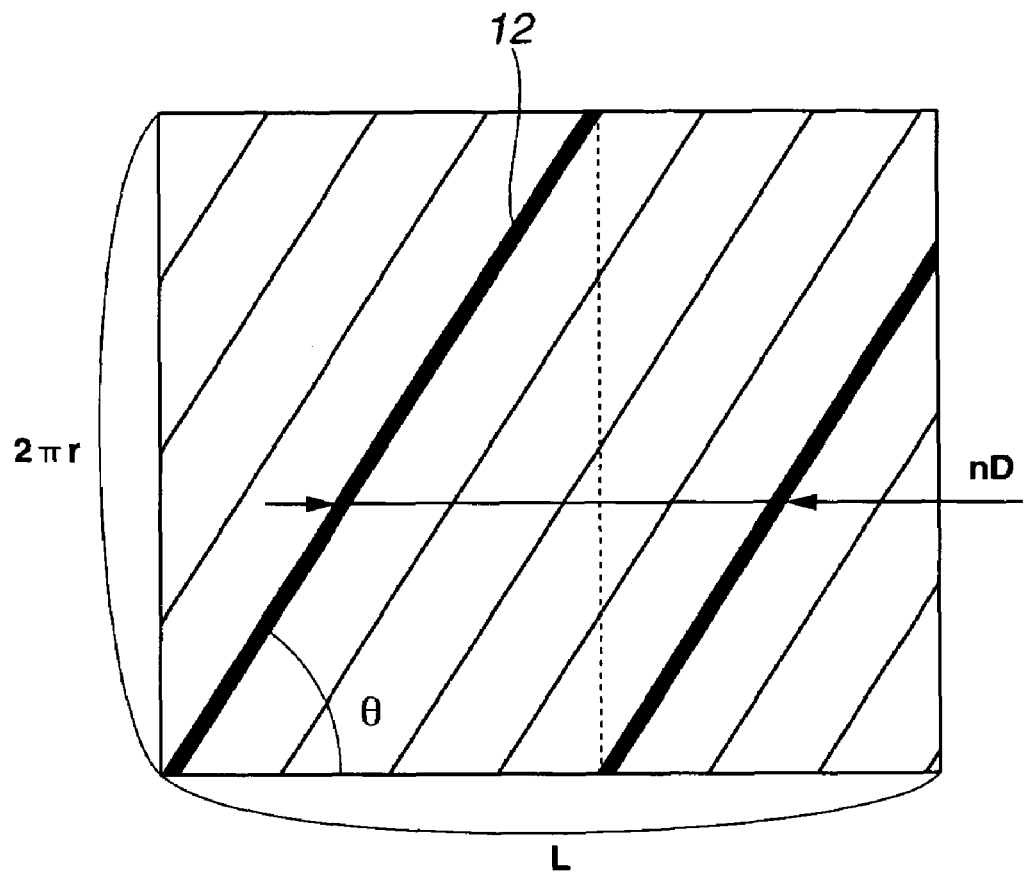
FIG. 18 is a developed view of an exterior cylindrical shape section of the medical device guidance system in FIG. 17.
Figure 19:
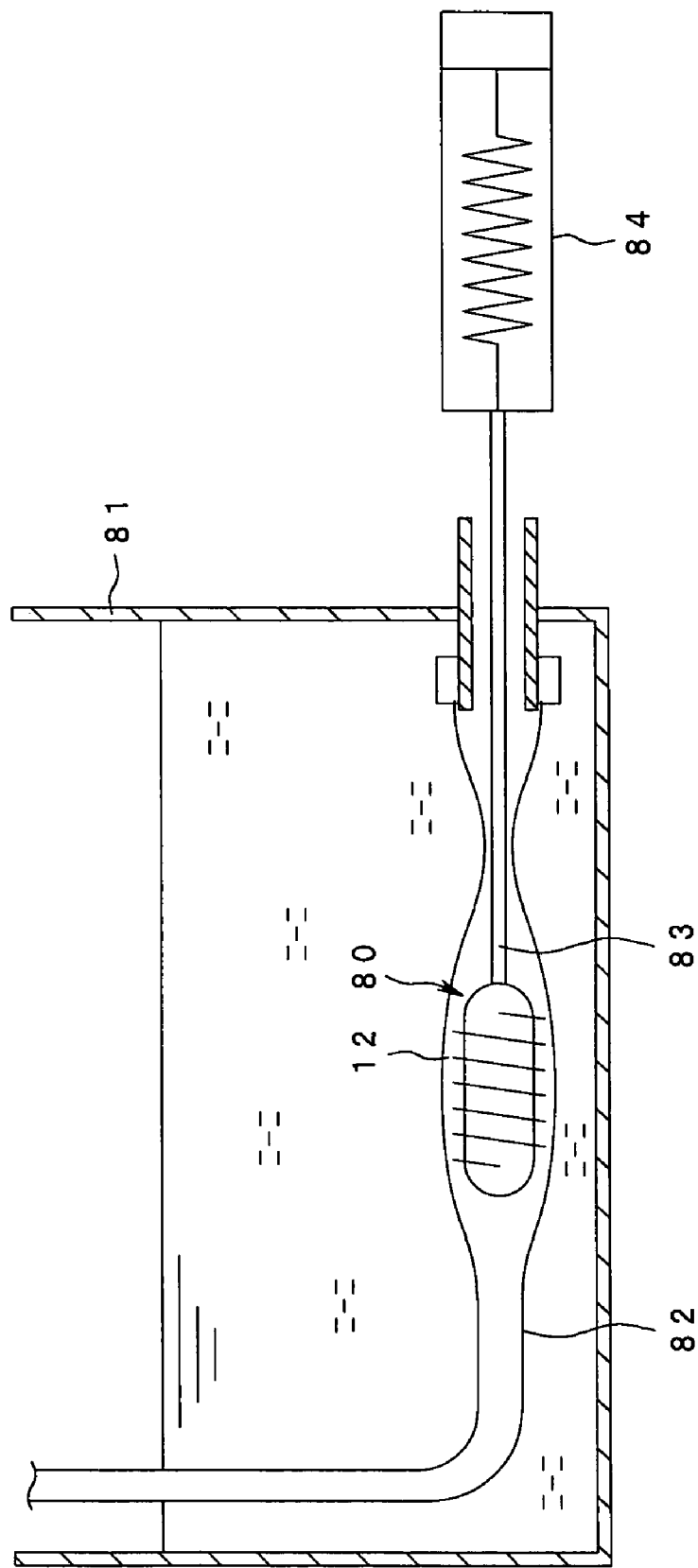
FIG. 19 is an explanatory view showing a state in which the propulsion speed of the medical device guidance system is measured by applying a rotating electromagnetic field.
Figure 20:
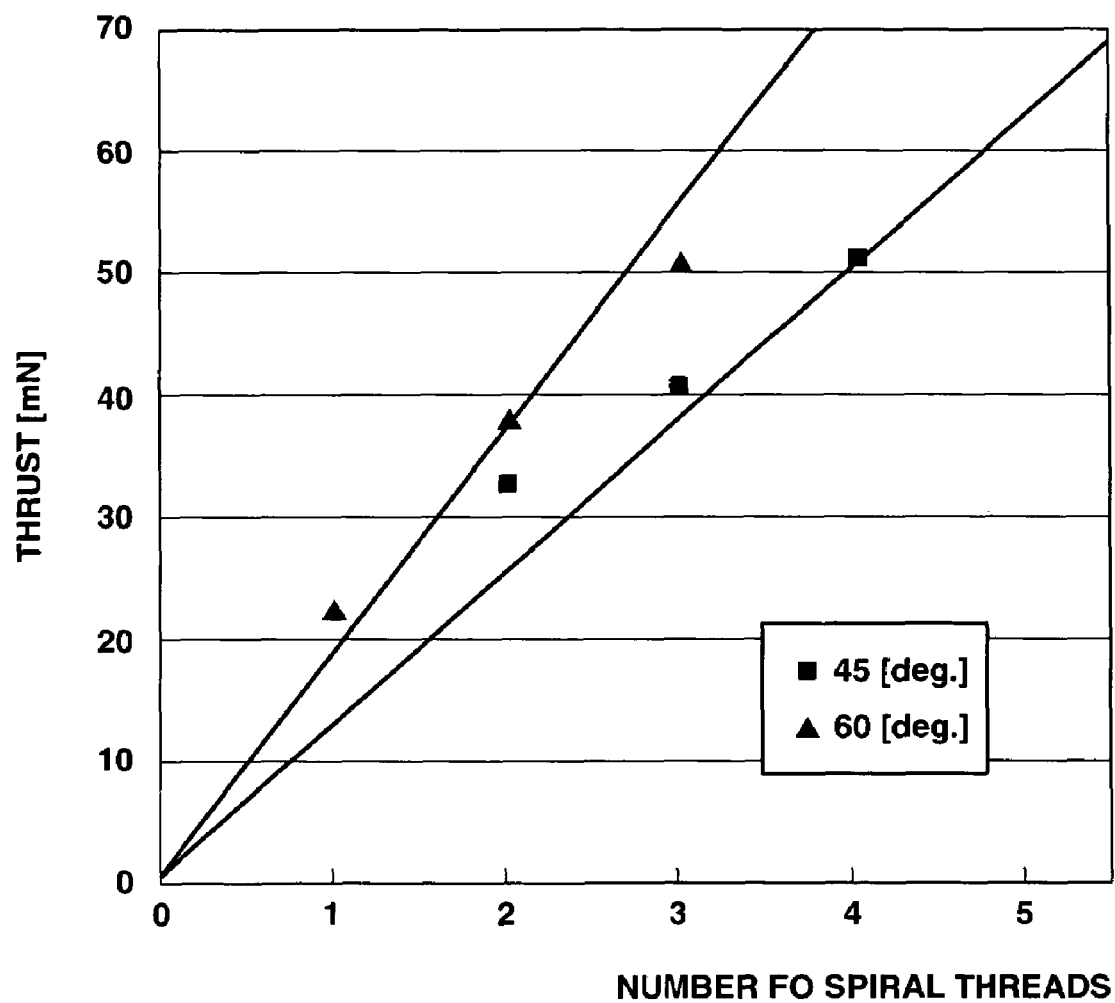
FIG. 20 is a graph showing thrusts (propulsion forces) plotted against numbers of threads, based on the measurement results in FIG. 19.
Figure 21:
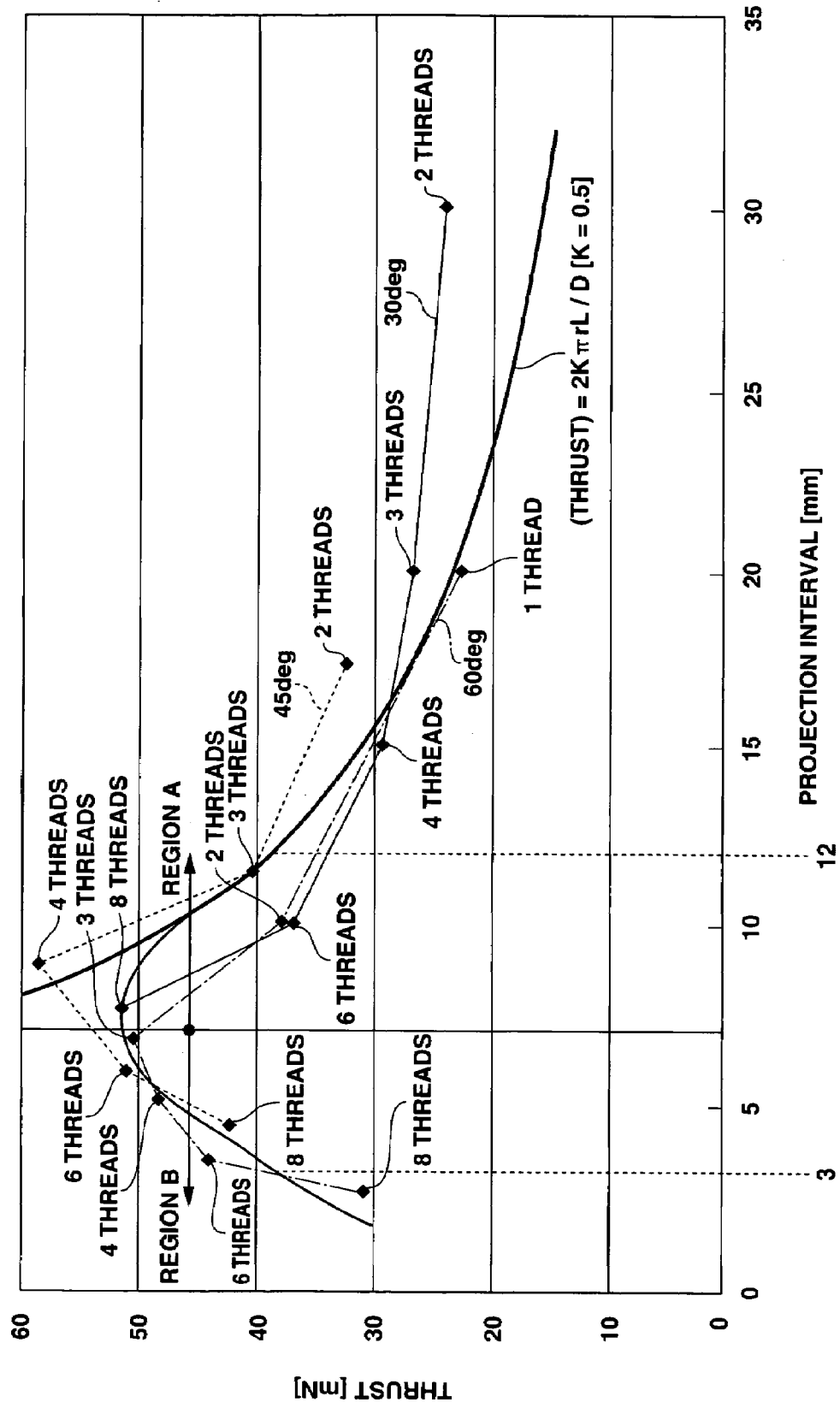
FIG. 21 is a graph showing thrusts (propulsion forces) plotted against projection intervals, based on the measurement results in FIG. 19.
Figure 22:
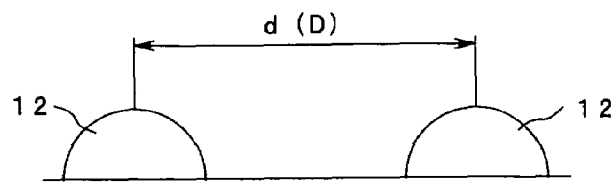
FIG. 22 is an explanatory view showing a spiral interval D when the cross section of the spiral projection is circular.
Figure 23:
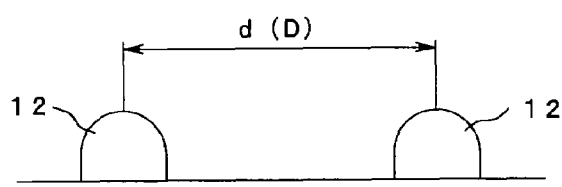
FIG. 23 is an explanatory view showing the spiral interval D when the cross section of the spiral projection is elliptical.
Figure 24:
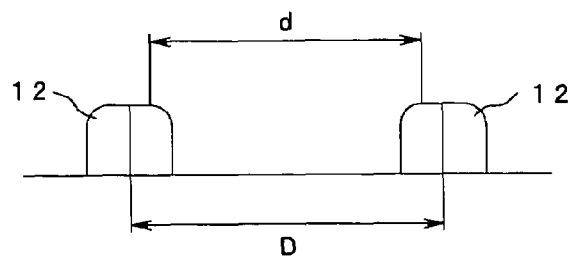
FIG. 24 is an explanatory view showing the spiral interval D and a projection interval d when the cross section of the spiral projection is a rounded rectangle formed by rounding the corners of a rectangle.
Figure 25:
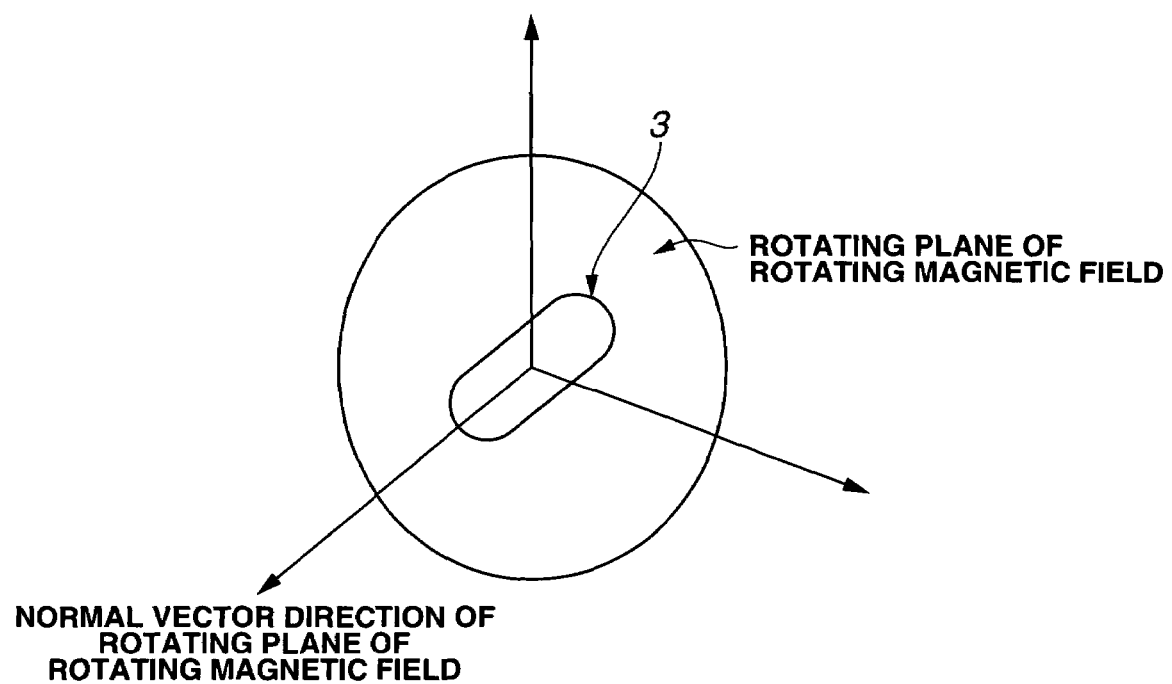
FIG. 25 is a diagram showing a propelling direction of the capsule in a rotating magnetic field represented by a Cartesian coordinate system.

FIGS. 1 to 25 relate to the embodiment of the present invention. FIG. 1 is a schematic block diagram showing the overall configuration of a medical device guidance system according to the embodiment of the present invention. FIG. 2 is a block diagram showing a more detailed configuration than that in FIG. 1. FIG. 3 is a side view showing the outer appearance of the capsule medical device main body. FIG. 4 is an explanatory side view of the main body of the capsule medical device. FIG. 5 is an explanatory front view of the main body of the capsule medical device in FIG. 4. FIG. 6 is a schematic configuration view of an operation input device. FIG. 7 is a schematic configuration view of a modification of the operation input device. FIG. 8 is a schematic configuration view of a modification of a stick in FIG. 6. FIGS. 9A and 9B are each a graph showing an example of signal waveform generated by a capsule rotational direction pattern generator, wherein FIG. 9A is a graph showing an example of signal waveform when the rotational directions are interchanged at set time intervals, and FIG. 9B is a graph showing an example of signal waveform when the capsule rotates in one direction always at a low rotational speed. FIG. 10 is an explanatory side view of the capsule medical device main body when it repeats an advance and a retreat based on the signal in FIG. 9A. FIG. 11 is an explanatory front view of the main body of the capsule medical device in FIG. 10. FIG. 12 is a schematic view showing of a state of the capsule medical device main body when making a turning motion based on the advance and retreat shown in FIG. 10. FIG. 13 is an example of a display device and setting menu. FIG. 14 is a modification of the setting menu in FIG. 13. FIG. 15 is a side view showing the outer appearance of a cable-equipped medical device having a flexible tube rotatably installed at the rear end thereof. FIG. 16 is a schematic side view showing a capsule medical device on which the pitch of a spiral projection is the same at the central portion, front end side, and rear end side. FIG. 17 is an explanatory side view showing parameters of the spiral structure section of the medical device guidance system. FIG. 18 is a developed view of an exterior cylindrical shape portion of the medical device guidance system in FIG. 17. FIG. 19 is an explanatory view showing a state in which the propulsion speed of the medical device guidance system is measured by applying a rotating electromagnetic field. FIG. 20 is a graph showing thrusts (propulsion forces) plotted against numbers of threads, based on the measurement results in FIG. 19. FIG. 21 is a graph showing thrusts (propulsion forces) plotted against projection intervals, based on the measurement results in FIG. 19. FIG. 22 is an explanatory view showing a spiral interval D when the cross section of a spiral projection is circular. FIG. 23 is an explanatory view showing the spiral intervals D when the cross section of the spiral projection is elliptical. FIG. 24 is an explanatory view showing the spiral interval D and a projection interval d when the cross section of the spiral projection is a rounded rectangle formed by rounding the corners of a rectangle. FIG. 25 is a diagram showing a propelling direction of the capsule in a rotating magnetic field represented by a Cartesian coordinate system.

As shown in FIGS. 1 and 2, the medical device guidance system (hereinafter abbreviated as "capsule guidance system") 1 according to the embodiment of the present invention includes a capsule medical device main body (hereinafter abbreviated as "capsule") 3 to be inserted into the body cavity of a patient (not shown) and functioning as a capsule endoscope picking up images of the inside of the body cavity; a rotating electromagnetic field generating device 4 arranged around the patient, i.e., outside the body and applying a rotating electromagnetic field to the capsule 3; an alternating-current power supply 5 for supplying an alternating-current power source for generating a rotating electromagnetic field to the rotating electromagnetic field generating device 4; a controller 6 arranged outside the body of patient and performing processing for wireless communications with the capsule 3, as well as controlling the alternating-current power supply 5 to control the direction and magnitude of the rotating electromagnetic field applied to the capsule 3; a display device 7 connected to the controller 6 and displaying images and the like picked up by the capsule 3. Furthermore, as operation input devices 8 connected to the controller 6 and inputting an instruction signal corresponding to an operation performed by an operator, the capsule guidance system 1 includes, for example, a direction input device 8a for generating a direction instruction signal with respect to the rotating electromagnetic field; a propulsion speed (or rotational speed) input device 8b for generating frequency instruction signal with respect to a rotating electromagnetic field corresponding to an operation, and a mode changeover switch 8c for switching a setting mode.

Also, the capsule guidance system 1 has a position/direction detector 9 for detecting electromagnetic waves from a position/direction detection antenna 18 (described later) incorporated in the capsule 3 and detecting the position and longitudinal orientation (or direction).

Moreover, the capsule guidance system 1 further has a setting device 10 for inputting a setting data for guiding the capsule 3 under a desired condition.

The capsule guidance system 1 is adapted to propel (or guide) the capsule 3 in a smooth and efficient manner by arranging the rotating electromagnetic field generating device 4 for generating a rotating electromagnetic field around the patient (not shown), controlling the alternating-current power supply 5 from the controller 6 side, and applying a rotating electromagnetic field to an electromagnetic field response section (described later) incorporated in the capsule 3 inserted in the body cavity tract of the patient, in a direction so as to propel the capsule 3.

The direction of rotating electromagnetic field by the rotating electromagnetic field generating device 4 can controlled by operating the operation input device 8 or the setting device 10 connected to the controller 6.

The position and longitudinal orientation (or direction) of the capsule 3 are detected by the position/direction detector 9, and after having subjected to image processing of the controller 6, they are displayed on the display device 7 as described later.

First, descriptions on the capsule 3 will be given below.

As shown in FIGS. 3 to 5, the capsule 3 has a substantially cylindrical or capsular shape, and a spiral projection (or screw section) 12 forming a spiral structure section for converting rotation into thrust, is provided on the outer peripheral surface of the exterior container 11 also serving as a body insertion section.

The spiral projection 12 is formed as a rounded cross-sectional structure of a substantially hemispheric shape on the outer peripheral surface of the exterior container 11, so as to be in smooth contact with inner wall surfaces in the body.

In the sealed inside of the exterior container 11, there are provided an objective optical system 13, an image pickup element 14 disposed at the image forming position thereof, and an illumination element 15 (refer to FIG. 1) providing illumination for photographing, and besides, a magnet 16 functioning as an electromagnetic field response section that exerts a force on a rotating magnetic field, or in a broad sense, on a rotating electromagnetic field, by responding to it.

The magnet 16 to be used here may be a permanent magnet, such as a neodymium magnet, samarium-cobalt magnet, ferrite magnet, iron-chromium-cobalt magnet, platinum magnet, alnico (Al—Ni—Co) magnet, or the like.

Rare-earth magnets such as the neodymium magnet and samarium-cobalt magnet have a strong magnetic force and have an advantage of allowing the size-reduction of a magnet incorporated in the capsule. On the other hand, the ferrite magnet is favorably inexpensive. Furthermore, the platinum magnet is superior in the anticorrosion characteristic.

This embodiment is arranged so that, as a rotating electromagnetic field, a rotating magnetic field is generated so as to act on the magnet 16 provided in the capsule 3. However, the arrangement may also be such that, as a rotating electromagnetic field, a rotating electric field is generated so as to act on a ferroelectric substance (not shown) provided in the capsule 3.

As shown in FIG. 4, the objective optical system 13 is arranged so that the optical axis thereof conforms with the center axis of the cylindrical capsule 3, so to speak, an insertion axis in the capsule 3. The objective optical system 13 is disposed, for example, inside a front-end cover 11a that is transparent and hemispherical, in the exterior container 11. As shown in FIG. 5, the central portion of the front-end cover 11a provides an observation window 17. While it is not shown in FIGS. 4 and 4, the illumination element 15 is arranged around the objective optical system 13.

In this case, therefore, the direction of visual field of the objective optical system 13 is an optical axis direction of the objective optical system 13, that is, a direction along the center axis C of the cylindrical section of the cylindrical capsule 3.

Inside the capsule 3, for example, in the neighborhood of the rear end of the exterior container 11, there is provided an antenna 18 for position/direction detection. This antenna 18 for position/direction detection is connected to an oscillator 19, and transmits a electromagnetic wave at predetermined timing.

By receiving this electromagnetic wave transmitted from the antenna 18 for position/direction detection, the position/direction detector 9 detects the position and longitudinal orientation (or direction) of the capsule 3.

Instead of this antenna 18 for position/direction detection, a coil incorporated in the capsule (not shown) may be provided to form a resonance circuit. In this case, the position/direction detector 9 generates an alternating magnetic field for generating a induced electromotive force, and detects a magnetic field generated by the resonance circuit that has generated the induced electromotive force by this alternating magnetic field, whereby the position and longitudinal orientation (or direction) of the capsule 3 is detected.

The magnet 16 is arranged in the neighborhood of the center in the longitudinal direction in the capsule 3, and as shown in FIG. 4, disposed so that an N-pole and S-pole are formed in a direction orthogonal to the center axis. The center of the magnet 16 is arranged to coincide with the barycentric position of the capsule 3. Therefore, upon applying a magnetic field from the outside, the center of a magnetic force acting on the magnet 16 becomes the barycentric position of the capsule 3. Thus, the capsule 3 is easy to be magnetically propelled in a smooth manner.

Also, as shown in FIG. 5, the direction of magnetization of the magnet 16, i.e., the direction of a dipole is arranged to conform with a specified arrangement orientation of the image pickup element 14.

Specifically, the image pickup element 14 is set so that the upward direction thereof when a picked-up image is displayed becomes a direction from the S-pole toward N-pole of the magnet 16.

The capsule guidance system 1 rotates the magnet 16 by applying a rotating magnetic field to the capsule 3 by the rotating electromagnetic field generating device 4. Thereby, the capsule guidance system 1 rotates the capsule 3 having therein the magnet 16 fixed, together with the magnet 16. Here, the spiral projection 12 provided on the outer peripheral surface of the capsule 3 is rotated in contact with the body cavity inner wall, thereby propelling the capsule 3.

In this embodiment, as shown in FIG. 3, regarding the spiral projection 12 formed on the outer peripheral surface of the capsule 3, the front end side thereof extends through the outer peripheral surface of the cylinder up to the side contracted into the shape of a hemisphere, and the front end 12a thereof is formed at a mid-way portion contracted into the hemisphere. Specifically, the end 12a is formed at a position outside an angle of view by the objective optical system 13.

On the other hand, the rear end 12b of the spiral projection 12 extends up to the neighborhood of the border between the outer peripheral surface of the cylinder and the side contracted into a hemisphere. In the example shown in FIG. 3, a spiral projection 12 is further provided in an intermediate position thereof, resulting in a double spiral.

As described above, when the capsule 3 having therein the magnet 16 incorporated is controlled by the rotating magnetic field, it can be known which direction is the upward direction of the image picked up by the capsule 3 from the direction of rotating magnetic field.

As shown in FIG. 2, besides the above-described objective optical system 13, image pickup element 14, magnet 16, position/direction detection antenna 18, the capsule 3 contains a signal processing circuit 20 for performing signal processing with respect to signals picked up by the image pickup element 14, a memory 21 for temporarily storing digital video signals generated by the signal processing circuit 20, a radio transmission circuit 22 for modulating video signals read from the memory 21 by a high-frequency signals to convert into signals to be radio-transmitted, and demodulating a control signal transmitted from the controller 6; a capsule control circuit 23 for controlling the capsule 3 including the signal processing circuit 20 and others; a battery 24 for supplying power source for operation to the electrical system inside the capsule 3.

On the other hand, the controller 6 includes a radio transmission circuit 25 for performing wireless communications with the radio transmission circuit 22 in the capsule 3; a data processing circuit 26 connected with the radio transmission circuit 25 and performing data processing and the like, such as image display with respect to image data transmitted from the capsule 3; a control circuit 27 for controlling the data processing circuit 26, the alternating-current power supply 5 and the like; and a storage circuit 28 for storing the state of rotating magnetic field functioning as a rotating electromagnetic field generated by the rotating electromagnetic field generating device 4 via the above-described alternating-current power supply 5, and more specifically, for storing information about the direction of the normal vector of a rotating magnetic field (hereinafter, abbreviated to as the "orientation of a rotating magnetic field") and the orientation of the magnetic field forming the rotating magnetic field.

A display device 7 is connected to the data processing circuit 26. The display device 7 displays images or the like that has been picked up by the image pickup element 14, and processed by the data processing circuit 26 through the radio transmission circuits 22 and 25. Because this data processing circuit 26 picks up images while the capsule 3 is being rotated, processing for correcting the orientation of the images when displayed on the display device 7 to be a definite orientation is performed, thereby performing image treating that allows images easily visible for the operator to be displayed (set forth in Japanese Patent Application No. 2002-105493).

The display device 7 can display the state of present rotating magnetic field, the state of function setting, and the position and direction of the capsule 3, obtained from the position/direction detector 9.

Inputted to the control circuit 27, are instruction signals corresponding to operations from the direction input device 8a and the propulsion speed (or rotational speed) input device 8b each constituting the operation input device 8, and the mode changeover switch 8c. The control circuit 27 is adapted to perform control operations corresponding to the respective instruction signals.

The control circuit 27 is connected with the storage circuit 28, and controls the storage circuit 28 to always store information about the orientation of the rotating magnetic field generated by the rotating electromagnetic field generating device 4 via the alternating-current power supply 5, and the orientation of magnetic field. Furthermore, after that, even when operations for changing the orientations of the rotating magnetic field and the magnetic field are performed, the control circuit 27 controls the storage circuit 28 to be able to continuously change the orientation of the rotating magnetic field or that of the magnetic field in a smooth manner. In short, the storage circuit 28 forms information providing means for the control circuit 27 when it performs a control operation.

Specifically, the instruction signal for an operation in the operation input device 8 serving as a first operation input means is inputted into the control circuit 27. The control circuit 27 outputs a control signal for generating a rotating electromagnetic field (or rotating magnetic field) corresponding to the instruction signal to the alternating-current power supply 5, and stores, into the storage circuit 28, information about the orientations of the rotating magnetic field and the magnetic field. Here, the storage circuit 28 may be disposed inside the control circuit 27.

Also, the control circuit 27 is connected to the position/direction detector 9, and receives information about the position and the longitudinal orientation (or direction) of the capsule 3, the information having been detected by the position/direction detector 9. By the information stored in the storage circuit 28 and the information detected by the position/direction detector 9, the control circuit 27 performs operations for generating a rotating magnetic field and/or controlling the orientations of the generated rotating magnetic field and the like.

The alternating-current power supply 5 connected with the control circuit 27 generates an alternating current, and includes an alternating-current generating and control section 31 comprising three alternating-current generating and control circuits for controlling the frequency and phase of the alternating current, and three driver section 32 comprising three drivers for amplifying respective alternating-current, respectively. The output currents from the three drivers are supplied to three respective electromagnets 33a, 33b, and 33c constituting the rotating electromagnetic field generating device 4.

The three electromagnets 33a, 33b, and 33c are each constituted of a pair of facing air-core coils, and are arranged to substantially orthogonally intersect one another. Because a uniform electromagnetic field can be generated in the space between the facing coils, an electromagnetic field can be generated in an arbitrary direction with the above-described arrangement. Preferably, each of the facing coils forms a Helmholtz coil.

It is arranged that an instruction signal for a magnetic field can be generated by operating the direction input device 8a constituting the operation input device 8 shown in FIG. 6; an instruction signal for a rotating magnetic field at a rotational frequency corresponding to the operation can be generated by operating the propulsion speed (or rotational speed) input device 8b; and the setting can be switched to a turning mode by operating the mode changeover switch 8c.

Specifically, the operation input device 8 includes the direction input device 8a formed of a joystick Sa projecting upward from the top surface of an operation box; the propulsion speed (or rotational speed) input device 8b formed of a stick Sb; and the mode changeover switch 8c formed of, for example, two buttons Ta and Tb.

Upon setting a Cartesian coordinate system as shown in FIG. 25, and representing the direction of the normal vector of a rotating plane of a rotating magnetic field, the direction of this normal vector becomes a propulsion direction of the capsule 3, and this direction can be set by a tilting operation of the joystick Sa.

In this case, by tilting the joystick Sa toward a front side, rear side, left side, and right side, it is possible to change the propulsion direction to the downside, upside, left side, and right side. The tilting amount in this case corresponds to the speed of angular change. If the joystick Sa is tilted to an intermediate direction, for example, a lower left direction or an upper right direction, the propulsion direction should be changeable to the corresponding directions.

Also, by tilting the stick Sb toward a front side, rear side, it is possible to set the rotational direction to the front side, rear side, respectively. Furthermore, it is arranged that the rotational frequency can be changed in accordance with a tilting angle.

The button Ta is a changeover button for selecting which input is to be enabled out of an input from the propulsion speed (or rotational speed) input device 8b and an input from the above-described setting device 10. On the other hand, the button Tb is a button for starting up a later-described graphical user interface (hereinafter, abbreviated as "GUI") by the setting device 10, that is, a button for displaying the GUI in a pop-up manner.

Therefore, the button Ta is adapted to switch a setting mode to the turning mode, while the button Tb is adapted to start up the GUI as a setting input to allow the input of the setting data by the setting device 10.

According to one modification shown in FIG. 6, the operation input device 8 may have a lever La that can be tilted to the top side of a joystick Sc as shown in FIG. 7 and that varies the rotational speed of the capsule 3 by varying the rotational frequency of the rotating magnetic field in accordance with the tilting amount; a button Tc for instructing about the rotational direction of the rotating magnetic field by an ON/OFF operation; and a mode changeover switch Td. In some case, the mode changeover switch Td may have the function of performing changeover to the turning mode and of starting up the GUI.

Then, the operation input device 8 can be operated by one hand, and the operability thereof is improved as compared with the case requiring a both-hand operation as shown in FIG. 6. Also, instead of the stick Sb shown in FIG. 6, for example, a foot switch F shown in FIG. 8 may be used to vary the rotational frequency in accordance with a degree of depression thereof.

In addition to the joystick and the foot switch, the operation input device 8 may include a personal computer or the like, and the operation may be performed by using a mouse, keyboard, GUI, and the like.

As shown in FIG. 2, the controller 6 includes a capsule rotational direction pattern generator 41 and mode changeover section 42 as an electromagnetic field pattern generating section.

The capsule rotational direction pattern generator 41 generates a rotational direction pattern signal based on setting data inputted from the above-described setting device 10.

As shown in FIG. 9A, this rotational direction pattern signal is a pattern signal in which the positive and negative polarities of signal intensity thereof are interchanged with respect to time. Detailed explanations about FIG. 9A and the subsequent drawings will be given later.

The output of the capsule rotational direction pattern generator 41 is connected to the mode changeover section 42. The propulsion speed (or rotational speed) input device 8b is also connected to the mode changeover section 42. In the mode changeover section 42, an output from the capsule rotational direction pattern generator 41 and a signal from the propulsion speed (or rotational speed) input device 8b are selectively received, and are outputted to the control circuit 27.

Usually, in the control circuit 27, the rotational direction and rotational speed of the capsule 3 are determined based on input from the propulsion speed (or rotational speed) input device 8b via the mode changeover section 42.

The maximum rotational speed at this time is not more than 5 Hz. The rotational speed during a usual operation is 5 Hz or less; preferably, 2 Hz or less; and more preferably, 1 HZ or less. By providing a setting function, the maximum rotational speed may be set to a value of 5 Hz or less.

Upon operating the mode changeover switch 8c and switching the signal outputted from the mode changeover section 42 to the signal from the capsule rotational direction pattern generator 41, the control circuit 27 performs control of the rotating electromagnetic field generating device 4 based on the output from the capsule rotational direction pattern generator 41.

It is preferable that the rotational speed at this time be not more than the maximum rotational speed obtainable by the input from the propulsion speed (or rotational speed) input device 8b. Furthermore, preferably, the rotational speed is not more than one half the maximum rotational speed; more preferably, not more than one fifth the maximum rotational speed; still more preferably, not more than one tenth the maximum rotational speed.

In the representation by the absolute frequency, preferably, the above-described rotational speed is 5 Hz or less, more preferably 1 Hz or less, and still more preferably 0.1 Hz or less.

Upon receipt of a signal shown in FIG. 9A, the capsule 3 performs movements for interchanging the rotational directions at set time intervals. Here, the instruction signal from the capsule rotational direction pattern generator 41 is a square-wave signal as shown in FIG. 9A. The positive polarity of an input signal with respect to the time axis corresponds to the advance of the capsule 3, while the negative polarity thereof corresponds to the retreat of the capsule 3.

In FIG. 9A, numerals denote the turn of advance/retreat. Here, (1) and (3) denote "advance" and (2) and (4) denote "retreat". By a rotating electromagnetic field (or rotating magnetic field) generated by this frequency instruction signal, the capsule 3 advances by a clockwise rotation and retreats by a counterclockwise rotation, and thereby performing movements as shown in FIGS. 10 and 11.

As shown in FIGS. 10 and 11, the capsule 3 repeats (1) advance, (2) retreat, (3) advance, and (4) retreat, and positions thereof stay within a definite range. In accordance with an input from the direction input device 8a in FIG. 6 or the joystick Sc in FIG. 7, the capsule 3 changes the orientation thereof. In other words, the capsule 3 is adapted to be able to turn while holding the positions thereof within a definite range.

A signal when, as shown in FIG. 9B, the capsule 3 rotates at a low rotational speed always in one way direction may be generated from the capsule rotational direction pattern generator 41. The rotational speed at this time is 1 Hz or less, and preferably 0.1 Hz or less. Because such a setting allows the capsule 3 to sufficiently slowly rotate, the capsule 3 changes the orientation thereof in accordance with the direction input device 8a in FIG. 6 and the joystick Sc in FIG. 7, virtually without the need to change the position thereof.

With such an arrangement, an effect similar to the foregoing can be produced, as well.

The control circuit 27 is connected to the setting device 10 so as to communicate therewith.

The setting information of the setting device 10 is written in the setting device 10 after it has been adjusted by the setting menu 53, functioning as the GUI shown in FIG. 13, or the setting menu 53B, functioning as the GUI shown in FIG. 14.

The data adjusted by the setting menus 53 or 53B is stored into setting device 10 via the control circuit 27. The control circuit 27 performs control based on data written in the setting device 10 as required. This control operation is executed at the times of the settings of rotational speed, turning speed, or the like.

In this embodiment, upon operating the button Tb of the mode changeover switch 8c, the GUI is displayed on the display device 7. According to an example of the setting menu 53B, the setting data at this time has two parameters: the rotational angle in one direction when "one backward rotation after one forward rotation" or "one half back rotation after one half forward rotation" is selected, and how much rotational speed is to be set.

Here, the button Tb of the mode changeover switch 8c is operated, and based on the outputted GUI starting signal, the display device 7, for example, displays, in a pop-up manner, a setting menu in the setting device 10, as shown in FIG. 13.

As shown in FIG. 13, the display screen of the display device 7 displays a capsule image 51 acquired by the capsule 3 and usually displayed, and the position and orientation image display section 52 on which the position and orientation of the capsule 3 in the body cavity is displayed.

The position and orientation image display section 52 displays the outline of a body shape of a patient. In the body shape, at an approximate position where the capsule main body 3 was detected, an icon arrow 52a indicating the position and direction of the capsule 3, acquired by the position/direction detector 9 is disposed. This icon arrow 52a indicates the approximate position of the capsule 3 by the position thereof, and indicates the longitudinal orientation (or direction) of the capsule 3 by the orientation thereof.

When operating the button Tb of the mode changeover switch 8c, the display screen of the display device 7 displays the setting menu 53 of the setting device 10. This setting menu 53 is a setting data input section of the setting device 10.

In the setting menu 53, a basic setting section 61 is disposed on an upper stage and a turning alone setting section 62 is disposed on a lower stage. The basic setting section 61 displays a rotational speed setting bar 61a for setting a rotational speed or the maximum rotational speed by the operation of the above-described propulsion speed (or rotational speed) input device 8b, as well as a turning speed setting bar 61b for setting a turning speed or the maximum turning speed by the operation of the joystick Sa of the above-described direction input device 8a.

The turning alone setting section 62 displays a rotational speed setting bar 62a for setting the rotational speed during the turning mode in which turning alone by the button Ta of the above-described mode changeover switch 8c, as well as a rotational angle setting bar 62b for setting the rotational angle. Here, when control is performed by the waveform in FIG. 9B, it suffices only to display the rotational speed setting bar 62a.

The ordinary operations in the basic operation are operations by the above-described joystick Sa in FIG. 6 and stick Sb. By these operations, the control circuit 27 generates a rotating electromagnetic field (or rotating magnetic field) in accordance with input from the joystick Sa and stick Sb and performs control such that ordinary operations of the capsule 3 are performed, based on the rotational speed or the maximum rotational speed, and turning speed or maximum turning speed of the capsule 3, set in the basic setting section 61.

The operations in the turning mode are operations for performing turning alone by the repetitions by the above-described advances and retreats by the depression operations of the button Ta. Also, the operations performed when performing control using the waveform as shown in FIG. 9B, operations for performing turning alone at a definite slow rotational speed.

By these operations, the control circuit 27 causes a rotating electromagnetic field (or rotating magnetic field) to occur in accordance with the rotational speed and rotational angle set in the turning alone setting section 62. Thereby, under inputs from the joystick Sa, the control circuit 27 performs control such that the capsule 3 performs a turning operation while holding positions thereof within a definite range.

Specifically, during the advance and retreat of the capsule 3 in the turning mode, the control circuit 27 performs control for generating a rotating electromagnetic field (or rotating magnetic field) so that the capsule 3 rotates at the rotational speed set by the turning alone setting section 62 and rotational angle set by the rotational angle setting bar 62b.

Here, as shown in FIG. 14, the setting menu may be arranged so that the turning setting section thereof can make more detailed setting.

As shown in FIG. 14, in the setting menu 53B, there is provided a turning alone setting section.

The turning alone setting section 62B displays the rotational speed setting bar 62a and turning speed setting bar 62c, and besides, a counterclockwise rotational angle setting bar 62d for setting the counterclockwise rotational angle, and a clockwise rotational angle setting bar 62e for setting the clockwise rotational angle.

Here, it is assumed that the clockwise rotation corresponds to an advance, and that counterclockwise rotation corresponds to a retreat. Then, the counterclockwise rotational angle setting bar 62d sets a rotational angle at the time of retreat, while the clockwise rotational angle setting bar 62e sets a rotational angle at the time of advance.

Then, the control circuit 27 performs control for generating rotating electromagnetic field (rotating magnetic field) so that the capsule 3 rotates at a rotational angle set by the clockwise rotational angle setting bar 62e, at the time of advance in the turning mode, and so that the capsule 3 rotates at a rotational angle set by the counterclockwise rotational angle setting bar 62d, at the time of retreat in the turning mode.

This enables the capsule 3 to be operable so as to be different in the rotational angle between advance and retreat in the turning mode.

Therefore, the control circuit 27 can perform control such that capsule 3 moves forward little by little, or moves backward little by little while repeating an advance and a retreat.

Such control allows the capsule 3 to change in position little by little in a lumen while changing the visual field direction of the capsule 3. Because, in a region to be observed in a more detail, the capsule 3 is to move slowly, an appropriate operation can be performed.

The operation in present embodiment with these features will now be described.

When the inside of a body cavity is inspected by the capsule main body 3, the patient swallows this capsule main body 3. When the capsule main body 3 swallowed into the body cavity passes through an esophagus and the like, it is illuminated by the illumination element 15, and an image picked up by the image pickup element 14 is sent to the extracorporeal controller 6 through the radio transmission circuit 22 by electromagnetic waves.

The controller 6 receives image data in the radio transmission circuit 25, and store demodulated image data in an image storage device, such as a hard disk provided in the inside of a data processing circuit 26, or the like, as well as performs display processing. Then, the controller 6 outputs the processed image signals to the display device 7, and displays, on the display device 7, the image data successively picked up by the capsule main body 3 as capsule images 51, as described above.

The position/direction detector 9 receives electromagnetic waves transmitted from the position/direction detection antenna 18 of the capsule 3, and outputs the received data to the controller 6. The controller 6 processes the received data from the position/direction detector 9, and calculated data on the position and longitudinal orientation (or direction) of the capsule 3, and image-processes the calculated data. Then, the data on the position and longitudinal orientation (or direction) that has successively been obtained is displayed on the position and orientation image display section 52 of the display device 7 as the icon arrow 52a, as described above.

The operator can recognize a current approximate position of the capsule main body 3 in the body cavity, from the image displayed on the display device 7. While watching the icon arrows 52a on the capsule image 51 and position and orientation image display section 52 each displayed on the display device 7, the operator operates the direction input device 8a and propulsion speed (or rotational speed) input device 8b so that the capsule main body 3 makes a desired movement.

Thereupon, the control circuit 27 performs control such that a rotating electromagnetic field (or rotating magnetic field) occurs in response to the operations with respect to the above-described direction input device 8a and propulsion speed (or rotational speed) input device 8b. The control circuit 27 causes the rotating electromagnetic field generating device 4 to generate a rotating magnetic field via the alternating-current power supply 5. Here, information about the generation of the rotating magnetic field is stored into the storage circuit 28.

When tilting operation with respect to the lever La or stick Sb is performed, a rotating magnetic field at a frequency corresponding to the tilting manipulated variable. Here, at starting and stopping times, the frequency may be gradually changed so as not to rapidly change in the rotational frequency of the capsule main body. Alternatively, both of the amplitude and frequency may be gradually changed.

In this manner, by applying the rotating magnetic field from the outside of the body, it is possible to rotate the capsule main body 3, and cause a magnetic torque to act on the magnet 16 incorporated in the capsule main body 3 inserted in the body to thereby rotate the capsule main body 3. At this time, in a state where the spiral projection 12 arranged on the outer peripheral surface of the capsule main body 3 is in contact with the inner wall in the body cavity, the capsule main body 3 can be speedily propelled as if a screw is rotated.

Herein, for example, there are cases where the capsule 3 is abutted against a haustra of colon in a large intestine, so that it gets stuck there.

Then, the operator performs an operation for executing the turning mode.

The operator depresses the button Tb and sets the turning mode by the above-described setting menu 53. Upon completing the setting input, the operator again depresses the button Tb and ends the setting. Then the operator depresses the button Ta of the mode changeover switch 8c, thereby entering the turning mode.

Thereupon, in the controller 6, the setting data from the setting device 10 is inputted into the capsule rotational direction pattern generator 41 and control circuit 27.

Based on the setting data inputted from the setting device 10, the capsule rotational direction pattern generator 41 generates a frequency instruction signal as shown in FIG. 9A, and outputs the instruction signal to the mode changeover section 42.

Based on a mode changeover signal outputted by the operation of the button Ta of the mode changeover switch 8c, the mode changeover section 42 switches the frequency instruction signal from the propulsion speed (or rotational speed) input device 8b, to a frequency instruction signal from the capsule rotational direction pattern generator 41, and outputs the switched signal to the control circuit 27.

Then, by the mode changeover section 42 switching from the propulsion speed (or rotational speed) input device 8b to the capsule rotational direction pattern generator 41, the control circuit 27 performs control such that the capsule 3 repeats an advance and a retreat, as well as performs turning control with respect to the capsule 3 under the operation by the joystick Sc or the joystick Sa.

If the signal generated by the capsule rotational direction pattern generator 41 is one as shown in FIG. 9B, the capsule 3 performs a low-speed rotation in one direction, and the control circuit 27 performs turning control of the capsule 3 under the operation by the joystick Sc or the joystick Sa.

The control circuit 27 generates a rotating electromagnetic field (or rotational magnetic field) corresponding to a signal from the capsule rotational direction pattern generator 41, and the joystick Sc or joystick Sa, by the rotating electromagnetic field generating device 4 via the alternating-current power supply 5.

Thereupon, for example, the capsule 3 advances under a clockwise rotation and retreats under a counterclockwise rotation, and thereby it repeats an advance and retreat with the positions thereof staying within a definite range as shown in FIGS. 10 and 11, and changes the orientation thereof for turning as shown in FIG. 12 under the input by the joystick Sc or joystick Sa.

If the signal generated by the capsule rotational direction pattern generator 41 is one as shown in FIG. 9B, the capsule 3 advances at a low speed under a clockwise rotation and retreats at a low speed under a counterclockwise rotation, and thereby it changes the orientation thereof for turning with the positions thereof staying under the input by the joystick Sc or joystick Sa.

Thereby, since the capsule 3 can turn virtually without the need to change the position thereof, it is possible to smoothly perform the direction change when the capsule 3 has been abutted against the haustra of colon or the like, the direction change has hitherto been difficult.

The capsule guidance system 1 according to this embodiment, therefore, is capable of improving the propulsion control characteristic.

Meanwhile, the capsule 3 according to this embodiment is of a cableless type that has neither line nor tube at the rear portion, but a cable-equipped capsule guidance system may be used in which a flexible tube is rotatably attached to the rear end of the capsule 3, i.e., on the opposite side of the front-end cover 39, as shown in FIG. 15.

As shown in FIG. 15, the capsule 3B has a cord, or a tubular guide member 70 having another end at the outside of the subject. This guide member 70 has a diameter of, e.g., 1 mm or more, and is a flexible member capable of being locked outside the subject.

In this case, combining the propulsion by the spiral projection 12 and the thrust/withdrawal by the guide member 70 enables the capsule 3 to be more effectively propelled/withdrawn.

This embodiment is constituted by incorporating the present invention into the capsule medical device main body functioning as a capsule endoscope, but the present invention is not limited to this. The present invention may also be applied to a tissue-acquiring type capsule medical device having acquisition means for acquiring a living body tissue, a drug discharge type capsule medical device for discharging drug, and a cauterization type capsule medical device for cauterizing a living body tissue.

In the movement control systems set forth in the above-described Japanese Unexamined Patent Application Publication Nos. 2001-179700 and 2002-187100, and the system set forth in the above-described Japanese Unexamined Patent Application Publication No. 2003-275170, in particular, parameters in respective spiral structure sections are not clearly described.

For this reason, in the conventional medical device guidance systems, the capsule medical devices thereof each have been difficult to obtain a sufficient thrust.

With this being the situation, detailed parameters for the spiral structure section will now be elucidated to obtain a sufficient thrust.

As shown in FIG. 16, regarding the pitch of the spiral projection 12 on the capsule 3, for example, the pitch "b" in the center portion of the capsule 3, having the largest outer diameter, is set to be equal to the pitch "a" in the front end side thereof, and the pitch "c" in the rear end side thereof, each having the diameters smaller than that of the center portion, namely, "a"="b"="c".

Furthermore, the spiral projection 12 on the capsule 3 will be optimized as described below.

As shown in FIG. 17, the spiral projection 12 has parameters, such as the cylinder section length L; cylinder section radius r; number of threads (represented by natural number); spiral interval D; spiral angle θ; spiral height h; spiral width b; and spiral groove width x.

First, the thrust of the capsule 3 was measured. FIG. 19 shows a measurement system.

FIG. 19 shows a water tank 81 for measuring the propulsion using a sample 80 simulating the spiral projection 12. In this water tank 81, a silicone tube 82 simulating a lumen organ is inserted in a state in which the first sample 80 having an exterior structure of the capsule 3 according to this embodiment is inserted into this silicone tube, and water is poured over the tube 82 to apply a water pressure thereto, the water level being, e.g., 20 cm.

The sample 80 is connected to a force gage 84 via the bar section 83, and this force gage 84 allows the measurement of thrust. Here, the sample 80 is rotatably arranged so as to run idle with respect to the bar section 83. In this state, the thrust was measured by applying a rotating magnetic field from the outside.

The specifications of the samples 80 used in the experiments are as follows: φ11 mm; cylindrical section length=2 mm; spiral height=1 mm; and spiral width=1 mm. As spiral angles and numbers of threads, the following combinations were employed.

| Spiral angle | Number of threads |
|---|---|
| 30[deg.] | 2, 3, 4, 6, and 8 |
| 45[deg.] | 2, 3, 4, 6, and 8 |
| 60[deg.] | 1, 2, 3, 4, 6, and 8 |

FIG. 21 shows thrust measurement results. FIG. 21 is a graph obtained by plotting spiral intervals of spirals on capsules 3 on the horizontal axis, and the measured thrusts on the vertical axis.

Depending upon the distribution of thrusts, there exist a region A where the reduction in spiral interval improves the thrust, and a region B where the reduction in spiral interval reduces the thrust.

Here, consideration will be given to the region A. First, regarding the capsules 3 described in the following list out of the capsules 3 of which the data is distributed in the region A, a graph obtained by plotting numbers of threads on the horizontal axis, and thrusts on the vertical axis is shown in FIG. 20.

| Spiral angle | Number of threads |
|---|---|
| 45[deg.] | 2, 3, and 4 |
| 60[deg.] | 1, 2, and 3 |

These results indicate that the thrust increases in proportion to the number of threads. The comparison among the capsules 3 with the same spiral angle indicates that the thrust increases in proportion to the entire length of a spiral.

Here, the entire length of spiral of the capsule 3 can be determined in the following method.

A developed view obtained by developing the exterior cylindrical section of the capsule 3 is shown in FIG. 18.

Based on the developed view of the exterior cylindrical section, the entire length is determined by the following expression:

entire length of spiral=$nL/\cos\theta$

Also, from the shape of spiral, the following expression is obtained.

$\tan\theta = 2\pi r/nD$

Here, the parameter contributing to the thrust is considered to be circumferential direction component of spiral.

Therefore, the thrust can be calculated by the following expression:

$$\text{Thrust} = K \times (\text{entire length of spiral}) \times \sin\theta \quad (1)$$
$$= KnL \cdot \tan\theta$$
$$= KnL \times 2\pi r/nD$$
$$= 2K\pi rL/D$$

Here, K is a proportionality constant.

From the forgoing, it can be seen that the thrust depends upon the radius of cylindrical section, the length of cylindrical section, and the spiral interval.

The comparison of these calculation results with the above-described measurement indicates that, in the region A in FIG. 21, the calculation results when the proportionality constant K is set to 0.5 in the above expression (1) conform very well with the corresponding measurement results.

Thus, when the spiral interval increases, the spiral length decreases, which results in a reduced thrust.

Next, the region B will be considered. It can be said that, in the region B, when the spiral interval decreases, living body tissues cannot enter the spiral, and hence, the effect of the spiral cannot be sufficiently exerted, thereby reducing the thrust.

Based on the above-described theorization, it can be said that, for the capsule 3 with a spiral height of 1 [mm], the spiral pitches of 3 to 12 [mm] enable the occurrence of a sufficient thrust.

Here, we will carry this consideration a step further, regarding the spiral interval when the spiral height changes.

The entering of the living body tissue into the spiral is approximated by the deflection caused by a tare weight of a double-end supported beam.

Herein, this beam is a double-end supported beam with a span l, the beam being subject to a uniform load w over the entire length thereof.

In this case, the deflection amount at the center portion caused by the tare weight (uniform load w) of the double-end supported beam is represented by the following expression:

Displacement=$5w \times l^4/384E \times I$

Here, when the spiral height becomes k times, in order that the displacement becomes k times, the following relational expression must be met.

$k \times$displacement=$5Wl^4/384EI$

Therefore, the span l can be obtained by the following expression:

$l = \sqrt[4]{(k \times \text{displacement}/P)}$

Here,
w: uniform load
l: width of beam (span)
E: modulus of longitudinal elasticity
I: geometrical moment of inertia
E×I: flexural rigidity Thereby, it is known that the spiral interval D required for the defection of living body tissue is proportional to the fourth root of the spiral height.

Therefore, the spiral interval D[mm] when the spiral height is h[mm], is within the following range:

$$3\times\sqrt[4]{h}[mm]<D[mm]<12\times\sqrt[4]{h}[mm] \quad (2)$$

In the above expression (2), depending upon the projection shape of the spiral projection 12, the spiral interval D is used, or the projection interval d is used instead of the spiral interval D.

If the cross section of the spiral projection 12 is circular of elliptical as shown in FIGS. 22 and 23, the spiral interval D is used, which is the distance between the center axes of mutually adjacent spiral projection portions 12.

On the other hand, if the cross section of the spiral projection 12 is a rounded rectangle formed by rounding the corners of the rectangle, the deflection of the living body tissue occurs at the starting point of the rounding portion. Therefore, instead of the spiral interval D, the projection interval d is here used, which is the distance between the starting points of the rounded portions of ellipses or substantial ellipses of mutually adjacent spiral projection portions 12, the starting points being located at the insides of the respective rounded portions.

In this case, the above expression (2) adopts the following expression, by using the projection interval d instead of the spiral interval D.

$$3\times\sqrt[4]{h}<d<12\times\sqrt[4]{h}$$

As a result, since the parameters of its spiral structure section can be clarified, the capsule 3 can achieve a sufficient thrust.

From the measurement results of thrusts in FIG. 21, when the capsule diameter is in the vicinity of φ11 mm (i.e., φ9 to φ13 mm) and the spiral width is about 1 mm, appropriate combinations of the numbers of threads with respect to the spiral angle are obtained as follows:

| Spiral angle | Number of threads |
| --- | --- |
| 30[deg.] | 8 |
| 45[deg.] | 3 or 4 |
| 60[deg.] | 4 or 5 |

Forming the spiral projection structure section so that the spiral angle becomes 40 degrees or more with respect to the symmetry axis relative to the advancing direction, improves the operability when modifying the orientation of the overall capsule guidance system.

Also, forming the spiral projection into 0.5 mm to 3 mm height prevents the diameter of the overall capsule guidance system from becoming too large, and allows the occurrence of a sufficient thrust.

Moreover, the above-described exterior has an substantially cylindrical section and a diameter changing section, and by forming the spiral structure section arranged on the diameter changing section and the spiral structure section arranged on the substantially cylindrical section at the same pitch, the thrust of the capsule medical device is enhanced. Simultaneously, equating the pitches of above-described both sections facilitates the manufacturing.

Embodiments structured by partially combining the above-described embodiment are also subsumed under the present invention.

The medical device guidance system and the capsule medical device according to this embodiment have an effect of improve the propulsion control characteristic.

What is claimed is:

1. A medical device guidance system comprising:
    a rotating electromagnetic field generating device for generating a rotating electromagnetic field for applying from the outside of a subject into the subject;
    a medical device main body inserted into a body cavity of the subject;
    an electromagnetic field response section provided in the medical device main body, and acting on the rotating electromagnetic field generated by the rotating electromagnetic field generating device;
    a controller for controlling the rotating electromagnetic field generating device to continuously change the state of the rotating electromagnetic field generated by the rotating electromagnetic field generating device;
    a rotational angle setting section for presetting rotational angles around a central axis of the medical device at which the rotational direction is to be reversed; and
    a rotating electromagnetic field pattern generating section for interchanging the rotating directions of the rotating electromagnetic field generated by the rotating electromagnetic field generating device based on each preset rotational angle, the interchange of rotating direction causing a repetitive advance and retreat of the medical device.

2. The medical device guidance system according to claim 1, wherein the set rotational angles are different between the advance and the retreat of the medical device main body.

3. The medical device guidance system according to claim 1, wherein the control device controls at least one of the rotational direction, the rotational phase, the electromagnetic field intensity, and the rotational frequency of the rotating electromagnetic field.

4. The medical device guidance system according to claim 1, wherein the medical device main body is a capsule medical device.

5. The medical device guidance system according to claim 1, further comprising: a rotational speed setting section for setting the rotational speed of the rotating electromagnetic field generated by the rotating electromagnetic field generating device.

6. The medical device guidance system according to claim 1, further comprising: an operation input device for generating instruction signals corresponding to an operation of an operator.

7. The medical device guidance system according to claim 6, further comprising: a mode changeover section for switching between at least one portion signal of the instruction signals generated by the operation input device and a signal generated in the rotating electromagnetic field pattern generating section.

8. The medical device guidance system as in claim 1, further comprising:
    a spiral structure section provided on the outer surface of the medical device main body, and converting a rotational movement generated by the electromagnetic field response section into a thrust.

9. The medical device guidance system according to claim 8, further comprising: an operation input device having a direction input device for generating a direction instruction signal, wherein, during the interchange of rotating direction, the control section controls the rotating electromagnetic field generating device to change the direction of the medical device, based on the direction instruction signal.

10. A method of operating a medical device guidance system, the method comprising the steps of:
displaying a setting menu;
changing a setting of an electromagnetic field pattern signal of an operation mode;
storing the setting of the electromagnetic field pattern signal of the operation mode; and
undisplaying the setting menu,
wherein the setting of the electromagnetic field pattern signal is a setting of a rotational angle with respect to a central axis of a medical device by which to interchange rotational directions of a rotating electromagnetic field, the rotational directions interchange producing a repetitive advance and retreat of the medical device.

11. The method of operating a medical device guidance system according to claim 10, wherein the rotational angle differs between advance and retreat of a medical device main body.

12. The method of operating a medical device guidance system according to claim 10, wherein the rotating electromagnetic field is controlled by at least any one of rotational direction, rotational phase, electromagnetic field intensity, and rotational frequency.

13. A method of operating a medical device guidance system, the method comprising the steps of:
changing an operation mode;
predefining rotational angles around a central axis of a medical device;
receiving an instruction signal; and
generating an electromagnetic field pattern signal in accordance with the instruction signal and the changed operation mode,
wherein at least one operation mode includes a mode for interchanging rotational directions of a rotating electromagnetic field based on the predefined rotational angles, the mode for interchanging rotational directions producing a repetitive advance and retreat of the medical device.

14. A method of operating a medical device guidance system, the method comprising the steps of:
displaying a setting menu;
changing a rotational angle setting of an electromagnetic field pattern signal of an operation mode, the rotational angle being with respect to a central axis of a medical device;
storing the rotational angle setting of the electromagnetic field pattern signal of the operation mode;
undisplaying the setting menu;
changing the operation mode;
receiving an instruction signal including the predefined rotational angles; and
generating the electromagnetic field pattern signal in accordance with the instruction signal and the changed operation mode,
wherein at least one operation mode automatically repeats an advance and a retreat of a medical device in accordance with the rotational angle setting.

15. The method of operating a medical device guidance system according to claim 14, wherein the operation mode includes a mode for interchanging rotational directions of a rotating electromagnetic field.

* * * * *